(12) United States Patent
Dixon

(10) Patent No.: US 8,655,043 B2
(45) Date of Patent: Feb. 18, 2014

(54) IMAGING SYSTEM WITH DYNAMIC RANGE MAXIMIZATION

(75) Inventor: Arthur E. Dixon, Waterloo (CA)

(73) Assignee: Huron Technologies International Inc., Waterloo, Ontario (CA)

( * ) Notice: Subject to any disclaimer, the term of this patent is extended or adjusted under 35 U.S.C. 154(b) by 135 days.

(21) Appl. No.: 12/993,010

(22) PCT Filed: May 15, 2009

(86) PCT No.: PCT/CA2009/000674
§ 371 (c)(1),
(2), (4) Date: Nov. 16, 2010

(87) PCT Pub. No.: WO2009/137935
PCT Pub. Date: Nov. 19, 2009

(65) Prior Publication Data
US 2011/0064296 A1    Mar. 17, 2011

(51) Int. Cl.
*G06K 9/00* (2006.01)
(52) U.S. Cl.
USPC .......................................... 382/133; 382/128

(58) Field of Classification Search
None
See application file for complete search history.

(56) References Cited

U.S. PATENT DOCUMENTS

| | | | | |
|---|---|---|---|---|
| 7,855,831 | B2* | 12/2010 | Wolleschensky et al. | 359/383 |
| 2005/0220342 | A1* | 10/2005 | Yamamichi | 382/171 |
| 2006/0031025 | A1* | 2/2006 | Staton et al. | 702/20 |
| 2006/0217913 | A1* | 9/2006 | Kaushikkar et al. | 702/107 |

OTHER PUBLICATIONS

Email COnversation with Mr.Daryl Schnurr dated Sep. 9, 2013.*

* cited by examiner

*Primary Examiner* — Nancy Bitar
(74) *Attorney, Agent, or Firm* — Daryl W. Schnurr

(57) ABSTRACT

A method of operating an instrument that is a macroscope, microscope, or slide scanner is provided where the instrument has a larger dynamic range for measurement than a dynamic range required in the final image of a specimen. In the method, data is measured from a specimen using the instrument, and the dynamic range of the measured data is contracted in the final image file during scanning.

10 Claims, 29 Drawing Sheets

IMAGING SYSTEM WITH DYNAMIC RANGE MAXIMIZATION

BACKGROUND OF THE INVENTION

1. Field of the Invention

This invention relates to the fields of confocal and non-confocal imaging of large microscope specimens with particular emphasis on scanning beam fluorescence and photoluminescence imaging systems, including multi-photon fluorescence, spectrally-resolved fluorescence, and second and third harmonic imaging. Applications include imaging tissue specimens, genetic microarrays, protein arrays, tissue arrays, cells and cell populations, biochips, arrays of biomolecules, detection of nanoparticles, photoluminescence imaging of semiconductor materials and devices, Raman imaging, and many others.

2. Description of the Prior Art

FIG. 1 shows one embodiment of a prior art confocal scanning laser macroscope, as described in U.S. Pat. No. 5,760,951. In this embodiment, the incoming collimated laser beam 102 from laser 100 passes through a beam expander (comprised of lens 104 and lens 106), and is expanded to match the diameter of entrance pupil 112 of laser scan lens 114 (note—entrance pupil 112 as indicated on the figure simply indicates the position of the entrance pupil. A real stop is not usually placed at this position). Scanning mirror 110 deflects the beam in the X direction. Laser scan lens 114 focuses the beam to spot 116 on sample 118, mounted on microscope slide 120, and light reflected from or emitted by the sample is collected by laser scan lens 114, descanned by scanning mirror 110, and partially reflected by beamsplitter 108 into a confocal detection arm comprised of laser rejection filter 130, lens 132, pinhole 134, and detector 136. Detector 136 is located behind pinhole 134. Light reflected back from focused spot 116 on sample 118 passes through pinhole 134 and is detected, but light from any other point in the sample runs into the edges of the pinhole and is not detected. The scanning mirror is computer-controlled to raster the focused spot across the sample. At the same time, microscope slide 120, which is mounted on a computer-controlled, motor-driven scanning stage 122, moves slowly in the Y direction. The combination of rapid beam scanning across the sample while it is moved slowly in the perpendicular Y direction results in a raster-scan motion of focused-laser spot 116 across sample 118. A computer, represented by computer screen 140, is connected to the detector 136 to store and display a signal from the detector 136. The computer provides means for displaying and storing the signal from the detector. This confocal macroscope has properties similar to those of a confocal scanning laser microscope, except that the field of view of the microscope is much smaller.

FIG. 2 shows a second embodiment of a prior art confocal scanning laser macroscope for simultaneous imaging of two different fluorophores. This instrument uses a two-laser or other two-wavelength source of collimated light, with the source wavelengths chosen to match the excitation wavelengths of the two fluorophores. If more than two fluorophores are present, additional laser wavelengths and detection arms can be added, or a spectrally-resolved detector can be used in a single detection arm. When imaging fluorescent nanoparticles, a single laser source can be used with multiple detection arms, or with a spectrally-resolved detector. A collimated light beam 102 from two-wavelength source 200 is expanded by a beam expander comprised of lens 104 and lens 106, and passes through dichroic filters 208 and 210 on its way to scanning mirror 110. Scanning proceeds as it did in the macroscope described in FIG. 1. Here, light emitted from both fluorophores travels back toward the two detection arms, with light from one fluorophore reflected by dichroic filter 210 into the second detection arm, comprised of laser rejection filter 230, focusing lens 232, pinhole 234 (placed at the focal point of focusing lens 232 in this infinity-corrected system) and is detected by detector 236. Light from the other fluorophore passes through dichroic mirror 210 and is reflected by dichroic mirror 208 into the first detection arm comprised of laser rejection filter 130, focusing lens 132, pinhole 134 and detector 136. Each detector sends an electrical signal proportional to the intensity of the light detected to an A/D converter (not shown) where the intensity of light detected at each pixel position for each fluorophore is converted to a digital value that is stored in an image file. Although many other detectors can be used, we usually use detectors that are comprised of a photomultiplier tube and a preamplifier. One of the advantages of this instrument when imaging multiple fluorophores is the ability to separately adjust the gain of each detector depending on the fluorescence intensity of that fluorophore.

FIG. 3 shows a third embodiment of a prior art scanning laser macroscope that images in brightfield in addition to fluorescence. In order to more clearly illustrate the transmission brightfield optics, the scanning stage is not shown in this diagram, however a scanning stage like that shown in FIG. 1 is used in this instrument. In the instrument described in FIG. 3 the multiple-laser source 300 provides red, green and blue laser wavelengths for RGB brightfield imaging and for exciting fluorophores, as well as one or more additional laser sources that can be used for exciting additional fluorophores. Brightfield imaging is accomplished by collecting the light that passes through specimen 118 and microscope slide 120. A large-NA collection lens 302 directs the transmitted light toward RGB detector 304 for recording the brightfield image. The output of detector 304 is sent to Computer 140 (as shown in FIG. 1). Each of the three colours (red, green and blue) are digitized (usually using 8 bits for each colour), resulting in a 24-bit RGB image. White balance can be adjusted by changing the gain in the Red, Green and Blue channels, or after imaging by adjusting the image data file.

Several other embodiments of the macroscope are presently in use. These include instruments for fluorescence and photoluminescence (including spectrally-resolved) imaging (several other contrast mechanisms are also possible), instruments in which the specimen stage is stationary and the raster scan is provided by two scanning mirrors rotating about perpendicular axes, non-confocal versions, and other embodiments. A macroscope with fine focus adjustment is described in U.S. Pat. No. 7,218,446 B2, and versions for reflected-light, fluorescence, photoluminescence, multi-photon fluorescence, transmitted-light, and brightfield imaging are described. The combination of a scanning laser macroscope with a scanning laser microscope to provide an imaging system with a wide field of view and the high resolution capability of a microscope is described in U.S. Pat. No. 5,532,873.

Several other technologies are used for imaging large specimens at high resolution. With tiling microscopes, the image of a small area of the specimen is recorded with a digital camera (usually a CCD or CMOS camera), the specimen is moved with a computer-controlled microscope stage, an image of the adjacent area is recorded, and so on until a number of image tiles have been recorded that together cover the whole area of the specimen. These image tiles can be butted together, or overlapped and stitched using computer stitching algorithms, to form one image of the entire specimen. Such images may contain tiling artifacts, caused by focus changes between adjacent tiles, differences in illumination intensity across the field of view of the microscope, and microscope objectives that do not have a flat focal plane.

When tiling microscopes are used for fluorescence imaging, the areas surrounding each tile and the overlapping edges of adjacent tiles are exposed twice (and the corners four times) which can bleach some fluorophores. Exposure is adjusted by changing the exposure time for each tile. If multiple fluorophores are imaged, a different exposure time is required for each, so each fluorophore requires a separate image at each tile position. Multiple exposure of the specimen for imaging multiple fluorophores can also increase bleaching. After all tiles have been collected, considerable effort (both human and computer) is required to stitch the tiles together and correct each tile for illumination intensity and collection sensitivity changes across the field of view of the microscope (correction for variations in illumination intensity and collection sensitivity is sometimes called "field flattening"). Stitching tiles together is also complicated by distortion and curvature of field of the microscope objective. The distortion and curvature are maximized near the edges of the field of view (just where stitching of tiles occurs).

Strip scanning instruments are also used for imaging large specimens. In these instruments, a short line of white light (about 1 mm long) is focused on the sample from above, and a linear CCD detector with 1000 or 2000 pixels is placed below the sample to collect light from each pixel position in the illuminated line in the specimen. Three separate linear detectors with appropriate filters to pass red, green and blue light are used for RGB brightfield imaging. The sample is moved in the direction perpendicular to the illuminated line to scan a narrow strip across the width of a microscope slide. The entire slide can be imaged by imaging repeated strips and butting them together to create the final image. Another version of this technology uses three linear TDI (time delay integration) sensors which increases both sensitivity and imaging speed. In both of these instruments, exposure is varied by changing scan speed.

Fluorescence imaging requires sensitivity that is thousands of times greater than for brightfield imaging, making it difficult to use the present strip-scanning instruments for fluorescence imaging, since they were designed for red, green and blue image channels with gains set to provide proper white balance in the final image, and equal exposure time for each channel. In fluorescence imaging, white balance has no meaning, and fluorescence imaging also requires large differences in exposure from one fluorophore to another, making it very difficult to use a strip-scanning instrument for simultaneous imaging of multiple fluorophores. In addition, for excitation of multiple fluorophores, it is useful to be able to choose a particular laser wavelength and intensity for excitation of each fluorophore. White light excitation is appropriate for brightfield imaging, but does not work well for multiple fluorophores (since the illumination includes wavelengths that overlap the fluorescence wavelengths being detected), or for fluorophores excited by wavelengths outside the wavelength range of white light (a good example is DAPI, a common fluorophore excited in the near UV).

When the macroscope is used for fluorescence imaging, it has several advantages. Exposure for each fluorophore can be adjusted separately without changing scan speed by changing either laser intensity and/or detector gain (in the case of a detector comprised of a photomultiplier tube (pmt) followed by a preamplifier, both the pmt voltage (which changes pmt gain) and preamplifier gain can be changed). The ability to adjust the detection gain for each fluorophore separately allows the instrument to simultaneously collect multiple fluorophore images that are all correctly exposed. In addition, the appropriate laser wavelength can be provided to excite a chosen fluorophore, and the excitation wavelengths can be chosen so they do not overlap the detection wavelength ranges.

Challenges for Imaging Very Large Specimens in Fluorescence

When very large specimens are imaged in fluorescence or in brightfield, file sizes are very large, which makes it difficult and time-consuming to store, view, process, analyze and transmit the resulting image data sets. For example, with one micron pixels and 8 bits per pixel, imaging the entire area of a microscope slide (2.5×7 cm) results in a 1.875 Gpixel image. If this is a brightfield image, with 24 bits per pixel (RGB), the resulting file size is 5.625 GB. If the resolution is increased by a factor of two to 0.5 micron pixels, the file size increases by a factor of four to 22.5 GB. 0.25 micron pixel size results in a 90 GB file.

In fluorescence imaging, the fluorescence intensity is often measured with a dynamic range of either 12 or 16 bits per fluorophore and stored as 16-bit data sets, so a 12-bit or 16-bit fluorescence image with three fluorophores requires a file size twice that of the greyscale brightfield image just described. Scanners for large microscopy specimens presently use pixels as small as 0.25 microns and microscope slides up to 5×7 inches in size. This combination results in a file size of 1.05 TB, even with only 24 bits per pixel.

File size limitations in some operating systems mean these data sets have to be broken up into multiple files for storage. Lossless (and sometimes lossy) compression is sometimes used to reduce the file size. A pyramidal file structure is often used, so that a small area of the image can be viewed at high resolution without loading the entire image into RAM. Although these large images can be stored in a pyramidal file structure that will allow the user to zoom in and roam around without loading the whole image into RAM, many image processing operations require the entire image file to be accessed, and some require the entire file to be loaded into RAM. If it is necessary to transmit large images to another location for analysis or storage, large bandwidth is required and the transmission time is long. Using a 100 GB file as an example, and a fiber network capable of transferring 1000 Mbps, if we assume a file transfer rate of 100 MBps, a 100 GB file would take 1000 seconds to transfer (about 17 minutes). At a download speed of 1000 kBps (a common download speed for high-speed internet connections), such a file would take 27.8 hours to transfer.

Most image processing and analysis operations require the entire file to be opened (at a USB-II hard drive file transfer rate of 500 Mbps it will take 27 minutes just to open a 100 GB file). Some image analysis programs (like Photoshop) open two copies of the image in RAM so changes can be made and previewed without having to access the stored file for every operation. This limits the size of image that can practically be analyzed using these programs to less than half the RAM available in the computer.

Before scanning a large specimen in fluorescence, it is important to set the exposure time (in a tiling or strip-scanning microscope) or the combination of laser intensity, detector gain and scan speed (in a scanning laser macroscope or microscope) so that the final image will be properly exposed—in general it should not contain saturated pixels, but the gain should be high enough that the full dynamic range will be used for each fluorophore in the final image. Two problems must be solved to achieve this result—the exposure (or gain) must be estimated in advance for each fluorophore, and for simultaneous detection of multiple fluorophores the exposure time (or gain) must be adjusted separately for each detection channel before scanning. For strip-scanning instruments, where exposure time is set by changing the scan speed, simultaneous detection of multiple fluorophores is very difficult if different exposures are required for each fluorophore.

SUMMARY OF INVENTION

For the purposes of this patent document, a "macroscopic specimen" (or "large specimen") is defined as one that is larger than the field of view of a compound optical microscope containing a microscope objective that has the same Numerical Aperture (NA) as the macroscope's scan lens.

For the purposes of this patent document the term "image acquisition" includes all of the steps necessary to acquire and produce the final image of the specimen, including but not limited to the steps of preview scanning, instrument focus and sample tilt, predicting and setting gain for imaging each fluorophore, image adjustments including scan linearity adjustment, field flattening (compensating for fluorescence intensity variation caused by excitation intensity and detection sensitivity changes along the length of the X scan), correction of fluorescence signal in one channel caused by overlap of fluorescence from adjacent (in wavelength) channels when two or more fluorophores are excited simultaneously, dynamic range adjustment, butting or stitching together adjacent image strips (when necessary), storing, transmitting and viewing the final image.

For the purposes of this patent document, the term "image processing" means all of the steps required to process the data to prepare the final image file, including but not limited to the steps of scan linearity adjustment, field flattening, correction for crosstalk when simultaneously scanning multiple fluorophores, correcting fluorescence image data by subtracting fluorescence originating from the glass of the microscope slide, subtracting the dark-current noise floor from the detector, and contracting the dynamic range of the image data to match the (smaller) dynamic range of the final image.

"Proper exposure" is defined as a gain setting such that in the output image file no (or only a small number of) pixels are saturated, and the dynamic range of the image data matches the dynamic range of the output image file (8 bits for an 8 bit file, 12 bits for a 12 bit file, etc.) and includes substantially the entire range of pixel amplitudes from the noise floor to the brightest pixel. The output image file may have a smaller dynamic range than that of the detection system, and that of the image file that is collected during scanning. This patent describes two methods of maximizing the dynamic range of data stored in the output image file—(1) accurately estimating the gain required to maximize the dynamic range of each detection channel when the dynamic range of the detection channel and the dynamic range of the output image data file are the same, and (2) using a dynamic range in the detection channel that is larger than that required in the final image data file and contracting the acquired data to utilize substantially the entire dynamic range of the final image data file. Where there are bright pixels that are not part of the required data set, such as from dust particles on the slide, or from position markers or areas not included in the required image, these pixels are not included in the calculation to maximize dynamic range. Using the entire dynamic range available is particularly important in fluorescence imaging, where variation in fluorescence intensity from one part of the image to another is often an important part of the data analysis. In addition, there is often a large difference in fluorescence intensity from one fluorophore to another, and it is very difficult (and important) to set the gain for each fluorophore to maintain the maximum dynamic range for each. This is especially true for fluorescence images of macroscopic specimens, since an image file that contains only 8 bits/pixel for each fluorophore is only half the size of an image with 12 bits/pixel (usually stored as 16-bit numbers) or 16 bits, and smaller file sizes can greatly reduce the time for image acquisition, storage, manipulation, analysis and transmission.

For the purposes of this patent document, the term "sparse image" means an image in which only pixels in a sparse grid exist in the image—e.g. one pixel at the centre of a square area of the image that would normally contain 100 or more pixels. The pixel values (intensities) are the same as they would be in the complete image, and do not reflect in any way the values of the pixels that were discarded (or not measured to produce the sparse image).

For the purposes of this patent document, the term "fluorescence imaging" shall be interpreted to include ordinary fluorescence imaging, multi-photon fluorescence, spectrally-resolved fluorescence, fluorescence in-situ hybridization (FISH), and other fluorescence mechanisms, and photoluminescence.

It is an object of this invention to provide a confocal or non-confocal imaging system for macroscopic specimens in which a rapid, sparse pixel preview image can be generated to direct setup of the imaging system and to provide information about the final scanned image before scanning.

RGB Brightfield Imaging:
  Acquire a sparse pixel preview image and generate red, green and blue histograms.
  The correct white balance in the preview image and in the final image can be set by adjusting the intensity of the red, green and blue detection channels so the peaks at the right side of the red, green and blue histograms are aligned.

Fluorescence Imaging:
  Acquire a sparse pixel preview fluorescence image for each detection channel
  Plot a histogram for each detection channel (fluorophore) based on the sparse pixel preview image
  Set exposure for each fluorophore to ensure that there is enough dynamic range to fill the dynamic range required in the final image
  Use histograms to direct and guide contraction of the data file for each channel during contraction into the final output image file.

It is an object of this invention to provide a photoluminescence wafer mapping system and method using a high-speed preview scan to predict the gross changes in photoluminescence across the wafer, to set exposure before the final scan, and to direct the operator to areas where high-resolution scans are required.

It is an object of this invention to provide a Raman imaging system for large specimens where a sparse pixel preview scan can be used to map changes in composition of the specimen at low resolution, and to direct the operator where to image small areas at high resolution.

It is an object of this invention to provide a method of estimating the gain required to maximize the dynamic range for each fluorophore in a fluorescence image before the final scan is started.

It is an object of this invention to provide a method of acquiring fluorescence images in which the image data from each fluorophore substantially fills the dynamic range available in the final image file, by estimating the gain required to maximize the dynamic range for each fluorophore in a fluorescence image before scanning, using detection channels that have larger dynamic range than that required in the final image, and contracting the dynamic range of the acquired data to fill substantially the entire dynamic range of the output image data file for each fluorophore.

It is an object of this invention to provide a confocal or non-confocal fluorescence imaging system for macroscopic specimens in which the correct gain setting for fluorescence imaging can be estimated from a rapid preview scan of the entire specimen (or part of the specimen) before the final scan is started.

It is an object of this invention to provide a confocal or non-confocal fluorescence imaging system for macroscopic specimens in which the correct gain setting for each fluorophore detection channel when simultaneously imaging multiple fluorophores can be estimated from a preview scan of the entire specimen (or part of the specimen) before the final scan is started.

It is an object of this invention to provide a multi-photon fluorescence imaging system for macroscopic specimens in which the correct gain setting for fluorescence imaging can be estimated from a preview scan of the entire specimen (or part of the specimen) before the final scan is started.

It is an object of this invention to provide a spectrally-resolved fluorescence imaging system for macroscopic specimens in which the correct gain setting for fluorescence imaging can be estimated from a preview scan of the entire specimen (or part of the specimen) before the final scan is started.

It is an object of this invention to provide a confocal or non-confocal fluorescence imaging system for imaging specimens containing fluorescent nanoparticles in which the correct gain setting for fluorescence imaging can be estimated from a preview scan of the entire specimen (or part of the specimen) before the final scan is started.

It is an object of this invention to provide a confocal or non-confocal fluorescence imaging system whereby a histogram of the output image data file is created and stored during scan.

It is an object of this invention to provide a confocal or non-confocal fluorescence imaging system whereby the value of the brightest pixel in the final image (or predetermined areas of the image) is measured and stored during scan.

It is an object of this invention to provide a method of contracting the dynamic range of the output image file from a scanner or microscope to substantially fill the dynamic range of an image file with smaller dynamic range than that originally output by the scanner or microscope.

It is an object of this invention to provide a method of using the data stored in the image histogram during scanning to contract the dynamic range of the image data file after scanning is complete, and to provide a method of performing such contraction either manually or automatically on the stored images of scan strips before the final image is assembled. This operation can be performed in the background while the next strip scan is underway.

It is an object of this invention to provide a method of using the preview image histogram to provide a method of performing dynamic range contraction and other image processing operations on the data stream during final scan, such that the image being stored during final scan has already been contracted to the dynamic range required in the output image file, and required image processing operations have been completed during scan.

It is an object of this invention to provide a confocal or non-confocal fluorescence imaging system for multiple fluorophores that corrects crosstalk between adjacent fluorescence channels on-the-fly during scanning, and method for correction of crosstalk between adjacent fluorescence detection channels on-the-fly when detecting multiple fluorophores.

It is an object of this invention to provide a means and method for fluorescence imaging of microarrays in which the correct gain setting and dark current offset can be estimated from a preview scan of the entire specimen (a sparse preview image) or part of the specimen.

It is an object of this invention to provide a means and method for fluorescence imaging of microarrays in which the correct gain setting and dark current offset can be estimated from a preview scan of the entire specimen (a sparse preview image) or part of the specimen, and perform dynamic range contraction automatically during scan. A histogram of the output image data file can be prepared automatically during scan and saved as metadata with the output image data file if desired.

It is an object of this invention to provide a means and method for imaging macroscopic specimens whereby a sparse image of the specimen is calculated during scanning and stored as metadata with the output image file. NOTE: This sparse image file can be used to suggest, direct and test additional image processing and analysis operations to be applied to the large output image file. For example, if the output image file is a 10 GB file, a sparse image file containing $1/100$ of the pixels in the original output image file is 100 MB in size, a file size that can easily and quickly be loaded into and processed by commercially-available image processing programs, and since it contains a fraction of the same pixels that are in the output image file, allows a rapid test to predict the outcome of some image processing algorithms that are planned for the output image file, allowing the operator to try different algorithms and settings without having to process the entire file. In addition, the sparse image file can be used by image storage and retrieval programs as a basis on which to calculate a smaller thumbnail (or the sparse image file, itself can be used as a thumbnail).

A method of operating a macroscope across a field of view that includes the entire specimen, the pixels having the same size and exposure as the same pixels would have in a final image if no changes were made to the detector gain or offset before scanning.

A method of operating an instrument that is a macroscope, microscope, or slide scanner, where the instrument has a larger dynamic range for measurement than a dynamic range required in a final image of a specimen, the method comprising measuring data from the specimen using the instrument, contracting the dynamic range of the measured data to use all or substantially all, of the dynamic range required in a final image file.

A method of operating a macroscope, microscope, or slide scanner to calculate, display and store as metadata information relating to a specimen, the method comprising calculating a histogram of the specimen while scanning the specimen, calculating a separate histogram for each fluorophore and attaching to a final image file a histogram of pixel intensity data in that image file.

A method of operating an instrument that is a macroscope, microscope, or slide scanner to systematically perform a dynamic range contraction of scanned image data of a specimen, the method comprising using a preview scanned histogram or data obtained from small-area scans to direct a dynamic range contraction process while simultaneously calculating a new histogram that describes data in a contracted file and saving the contracted file with a new histogram included as metadata.

A method of operating a macroscope, microscope, or slide scanner to perform a series of data processing steps during scanning of a specimen, the method comprising contracting a dynamic range of an image of the specimen and correcting one or more properties of the macroscope, microscope, or slide scanner selected from the group of correcting dark current noise, flat field, background fluorescence from a glass slide for the specimen and correction of overlap between adjacent fluorescent channels, and making all corrections during scanning.

A method of scanning microarrays of a specimen using a macroscope, microscope, or slide scanner to scan microarrays using a detector having a dynamic range larger than that required in an output data file, the method comprising automatically performing a dynamic range contraction of the scanned image data during scanning using a preview scan histogram or data obtained from small-area scans to direct the dynamic range contraction process, simultaneously calculating a new histogram that describes the data in a contracted file and saving the contacted file with a new histogram included as metadata.

A method of scanning a specimen using a macroscope, microscope, or slide scanner having a detector with a dynamic range that is larger than that required in an output data file and using one of RGB brightfield imaging, fluorescence imaging and Raman imaging, said method comprising acquiring a sparse pixel preview image for each detection channel in generating a histogram for each detection channel based on the sparse pixel preview image, using histograms to direct and guide contraction of a data file for each channel used during contraction into a final output image file and generating the final image.

A method of scanning a specimen using a macroscope, microscope, or slide scanner to scan the specimen having a detector with a dynamic range which is larger than that required in an output data file, the method comprising automatically performing a dynamic range contraction of the scanned image data during scanning, using a preview scan histogram or data obtained from small-area scans to direct the dynamic range contraction process, simultaneously calculating a new histogram that describes the data in a corrected file and saving the contracted file with a new histogram included as metadata.

DETAILED DESCRIPTION OF A PREFERRED INVENTION

When microscopes are used to image small specimens, improper exposure of one or more channels can easily be fixed by changing the gain and scanning again. When large specimens are scanned, it is important to predict the exposure accurately before scanning. The current version of the macroscope scans at 1/40 second per line, with up to 40,000 pixels per line. At that rate, it stores 1,600,000 pixels per second, and data that fills a 100 GB file is collected in 5.8 hours (24 bits per pixel). It is no longer practical to change the gain and scan again!

In fluorescence microscopy, field flattening (the process of adjusting the final image to correct for uneven illumination and detection sensitivity across the field of view); background correction to remove fluorescence from the glass in the microscope slide from the final image; and correction for crosstalk between adjacent (in wavelength) fluorescence channels are image processing operations that are performed after scanning (or collecting image tiles) is completed. All of these operations increase the time for preparing the final image and in some cases will take as long to perform as the original image did to acquire. These three image data corrections are discussed below:

1) Field Flattening:

In fluorescence microscopy, flat-field correction is required to correct the image data for changes in illumination intensity and detection sensitivity across the field of view. Microscopes using a 2-d CCD array require a 2-d correction across the entire image (and tiling systems require each tile to be corrected before stitching). Strip-scanning microscopes that use a linear CCD or a TDI CCD require a 1-d flat-field correction across each strip. Raster-scanning (beam-scanning) laser microscopes also require a 2-d correction across the image or across each image tile if they are used for tiling, and scanning-beam/scanning-stage microscopes or macroscopes require correction across each strip. When separate scanning lasers are used for different fluorophores, each combination of laser, fluorophore and detection arm should be calibrated separately.

One way to estimate the correction required is to scan a specimen that has constant fluorescence intensity across its width.

Figure 1:
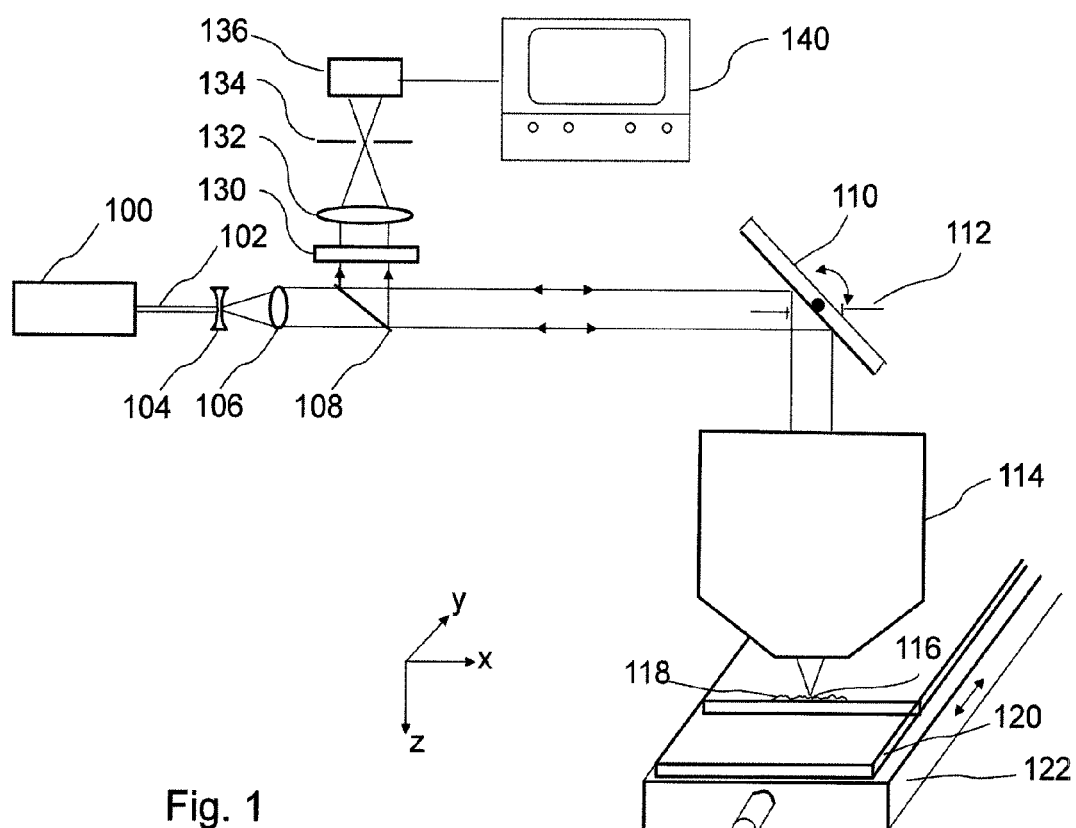
FIG. 1 is a schematic view of a prior art confocal scanning-beam/scanning-stage optical macroscope.
Figure 2:
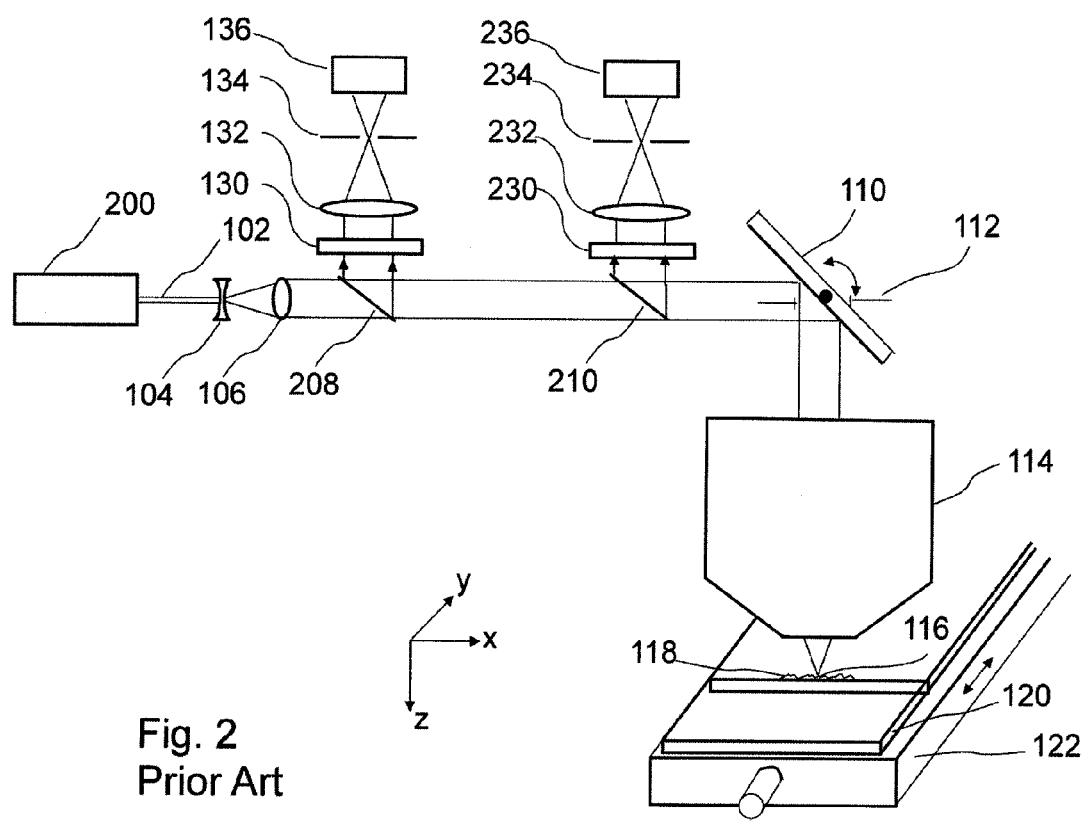
FIG. 2 is a schematic view of a prior art confocal scanning-beam/scanning-stage macroscope for simultaneous imaging of two fluorophores.
Figure 3:
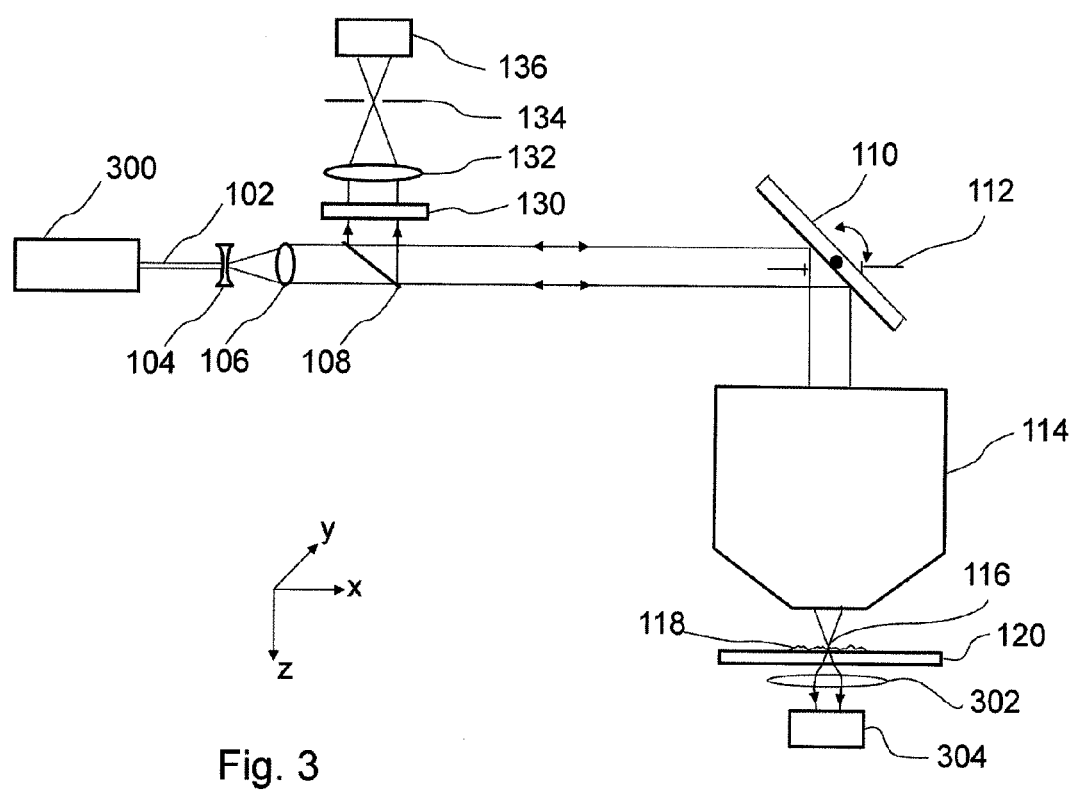
FIG. 3 is a schematic view of a prior art confocal scanning-beam/scanning-stage macroscope having both a confocal detection arm for fluorescence imaging and a transmission detector for brightfield imaging.
Figure 4:
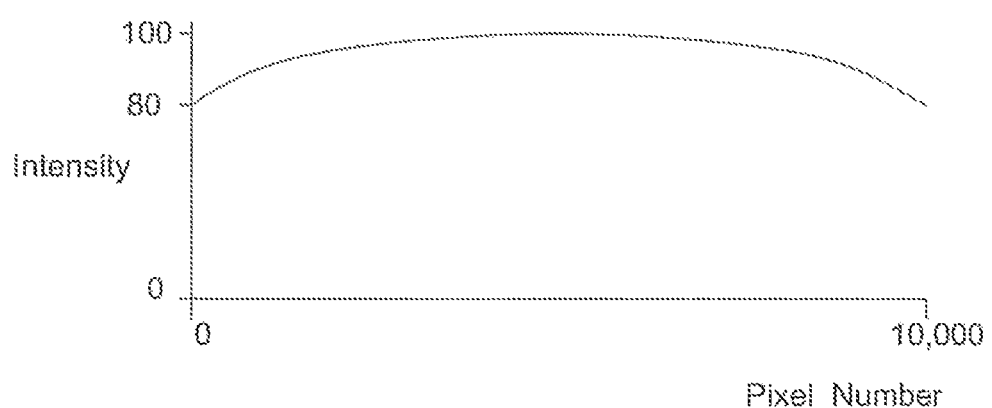
FIG. 4 shows a plot of fluorescence intensity vs. pixel number along the length of a scan (not from a real sample)

FIG. 4 shows a plot of fluorescence intensity vs. pixel number along the length of a scan (not from a real sample). In a real specimen, the change in measured fluorescence intensity is not expected to be as large as that shown, and the plot is usually not perfectly symmetric. The nonlinearity is caused by changes in illumination intensity and optical collection efficiency along the length of the scan. Usually the curve is flat near the center, and drops off at the edges because of the onset of vignetting near the edges of the field of view of the laser scan lens (and intermediate optics), and a reduction in telecentricity of the scan lens at the ends of the scan. These curves assume that a correction for detector dark current has already been made, either by bringing the dark current noise floor to zero by applying an offset voltage to the preamplifier, or digitally by subtracting the noise floor value from the measured intensity values. The noise floor value is expected to be constant along the scan line. Also, because of differences between pmt's (and other detectors), each detection arm should be calibrated and corrected separately.

Flat field correction is applied on a pixel by pixel basis along the length of a scan line, and may be applied either to increase the pixel values to match the maximum pixel values near the centre of the scan, or to reduce the values at the centre to match those at the end.

When imaging a real specimen, the value of pixels measured during fluorescence scanning for each combination of laser, fluorophore and detection arm should be multiplied by a flat-field correction factor (FFc) as follows:

$$FFc(i) = Fm(i) * \{1 - (Fm(i) - Fmin)/Fmax\} \quad (1)$$

The data shown in FIG. 4 generates a set of correction factors ranging from 1 (for the pixels i=1 and i=10000) to 0.8 (for pixel i=5000). This set of calibration factors is applied to each scan line on a pixel-by-pixel basis after the image has been collected.

$FFc(i)$=correction factor value for pixel i, where i goes from 1 to 10,000 (for a scan length of 10,000 pixels, or to the end of the scan when the number of pixels is different from 10,000), And for this calibration scan, $Fm(i)$ is the intensity value for the fluorophore measured at pixel position i, $Fmax$ is the intensity of the brightest pixel in the scan range (in this example, Fmax=1000), and $Fmin$ is the intensity of the dimmest pixel in the scan range (in this example, Fmin=800).

NOTE: The flat field calibration factors described above are defined such that the line intensity near the centre of the line is reduced during flattening. It is also possible to increase values near the ends of the line so the values of pixels near the end of the line are increased, and those near the centre are not decreased.

NOTE: A separate field flattening correction must be measured for each laser, filter set and detection arm, and applied to the fluorescent images acquired with this scanning combination.

2) Correcting Images for Background Fluorescence from the Slide:

In fluorescence microscopy, there is often small background fluorescence from the glass in the microscope slide, and it is important to measure and remove this signal. One solution to the background fluorescence problem is to eliminate background fluorescence by using microscope slides that do not fluoresce. Quartz slides are available that do not fluoresce even when illuminated in the near ultraviolet, but they are very expensive. Plastic slides fluoresce more than glass, but are quite inexpensive and may be useful in certain applications if this fluorescence can be easily removed from the image data. Confocal scanners (like the confocal macroscope) reject signals from above and below the plane of focus, so background fluorescence from the slide is reduced, although it is still not eliminated completely.

Figure 5:
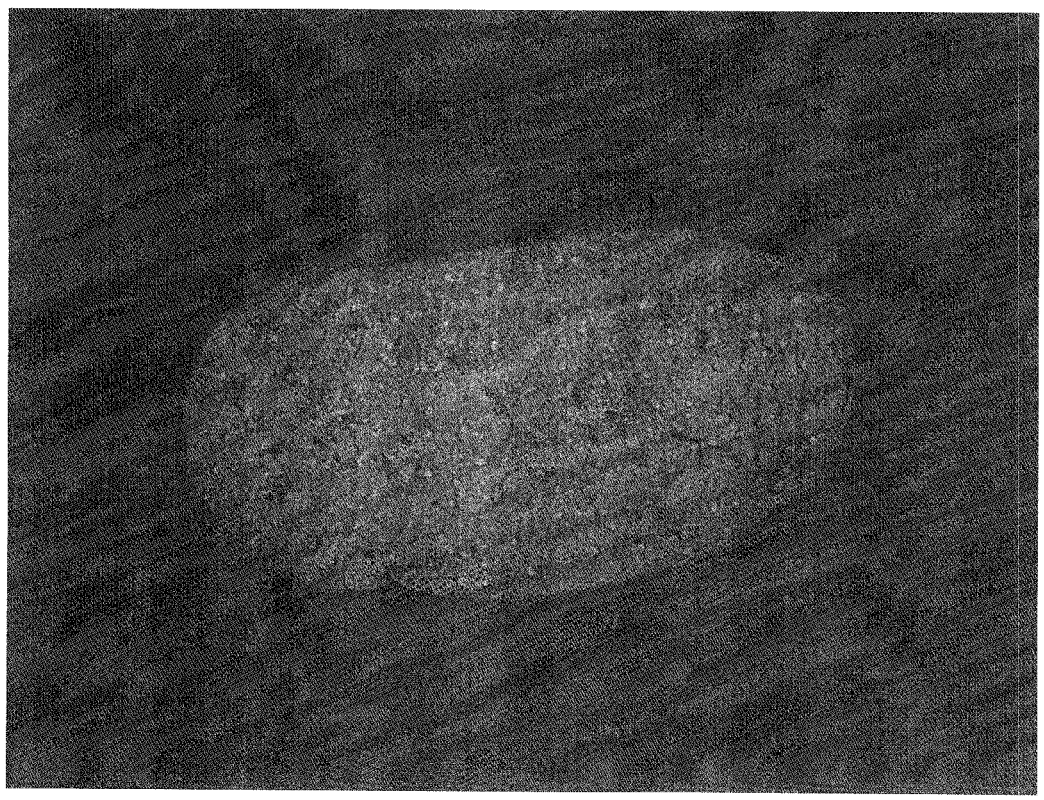
FIG. 5 is a fluorescence image from a strip scanner.

FIG. 5 is a fluorescence image from a strip scanner. The specimen was quite old and fluorescence was weak, but it makes a great image to show background fluorescence from the slide.

Figure 6:
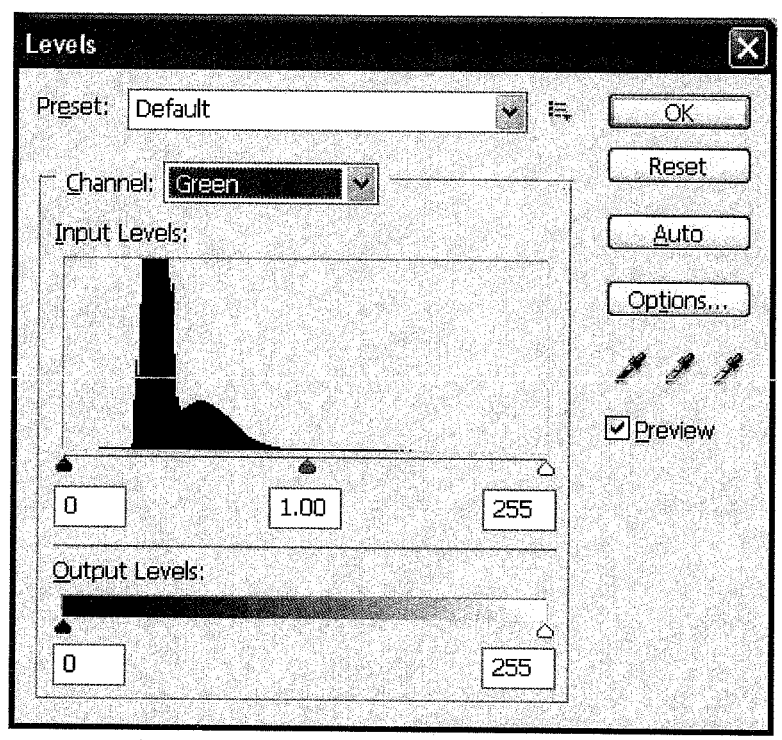
FIG. 6 is the green histogram for the image in FIG. 5, measured in Photoshop.

FIG. 6 is the green histogram for the image in FIG. 5, measured in Photoshop. Note there is a huge peak at low intensities, probably from the fluorescent background of the slide. Also important—this is supposed to be an 8-bit image, which should have 256 levels filled with data. Most of the data in this image is between level 35 and level 115, and levels below 19 and above 180 are completely empty. This is really a 6-bit image, not an 8-bit one.

In order to get a better idea of the data histogram for the specimen itself, the image in FIG. 5 was cropped to remove most of the empty area. The cropped version of FIG. 5 is shown in FIG. 7.

Figure 7:
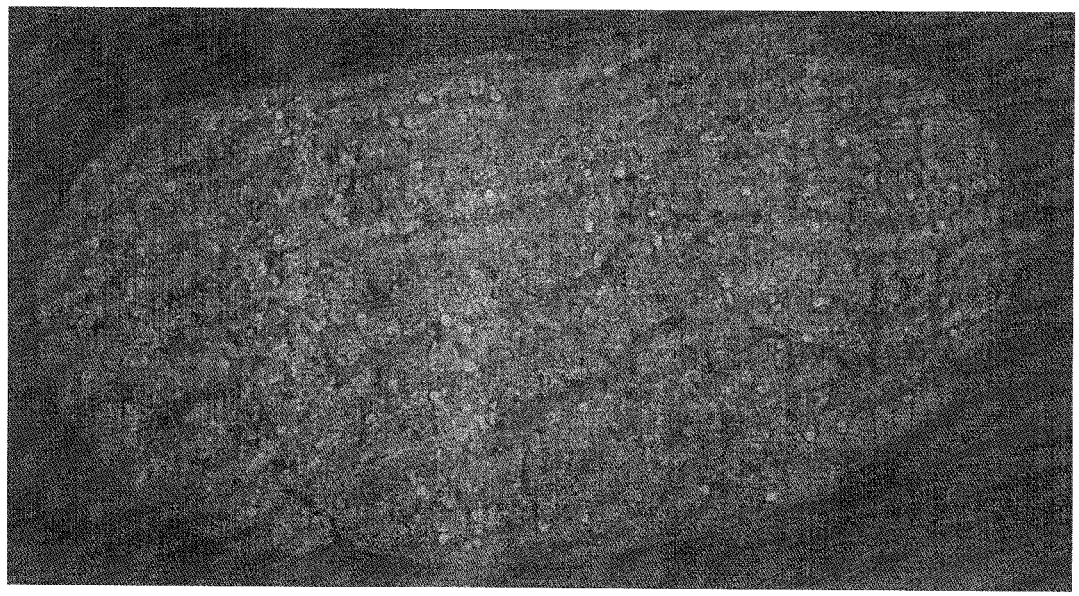
FIG. 7 is a fluorescence image from a strip scanner of the image in FIG. 5 cropped to enclose the specimen.

FIG. 7 is the cropped version of FIG. 5. A second version of FIG. 7 has been added to the end of the Application with a greater contrast between the specimen and the background fluorescence.

Figure 8:
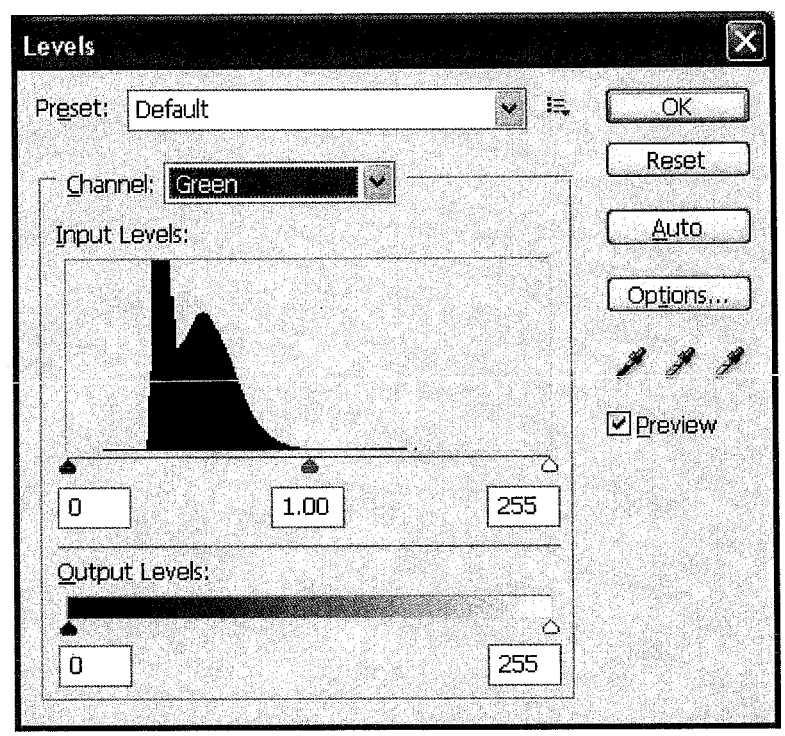
FIG. 8 is a cropped area from the bottom of FIG. 5 showing only the background fluorescence.

FIG. 8 is a histogram for FIG. 7. Note that this cropped version has a much smaller peak on the left hand (low intensity) side, indicating that the large peak in the un-cropped version comes from the background fluorescence in the area that was cropped out.

Figure 9:
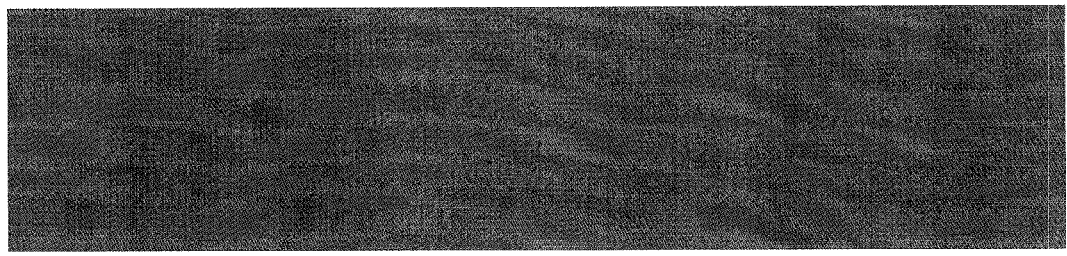
FIG. 9 is a cropped area from the bottom of FIG. 5 showing only the background fluorescence.

FIG. 9 is a cropped area from the bottom of FIG. 5 showing only the background fluorescence. The background signals that appear in this empty area of the microscope slide also are added to the signals where there is tissue and should be subtracted from signals measured in the area of the microscope slide that is covered with tissue.

Figure 10:
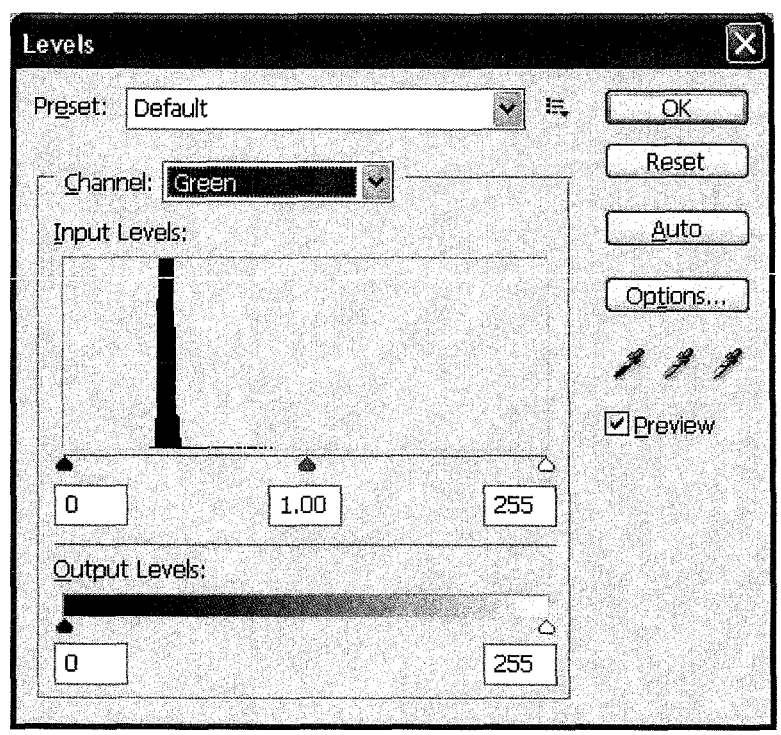
FIG. 10 is a histogram of the image in FIG. 9 showing a peak from the fluorescence background. The unfilled levels on the left-hand side are caused by an incorrect setting of offset in the detector.

FIG. 10 is a peak from the fluorescence background. The unfilled levels on the left-hand side are caused by incorrect setting of the offset current at the detector.

Figure 11:
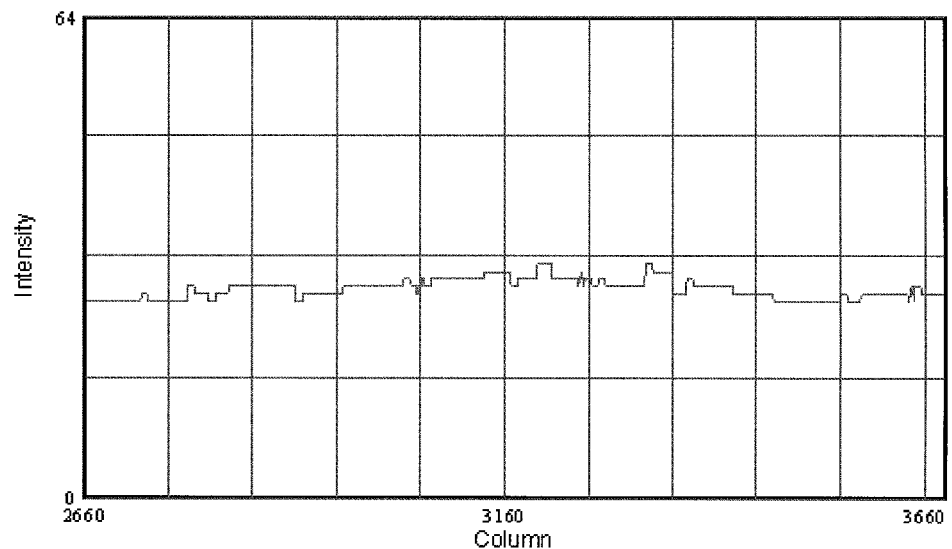
FIG. 11 is a background signal measured for approximately one line scan width across one of the nine strips in the image in FIG. 9.

FIG. 11 is background fluorescence measured for approximately one line scan width across one of the nine strips in the image in FIG. 9.

The image in FIG. 5 has an 8-bit dynamic range—this data shows that the bottom 30 levels in the dynamic range contain no information about the specimen—only dark-current noise, offset current, and background fluorescence from the glass microscope slide. The entire image data set shown in FIG. 5 should have been corrected by subtracting from each pixel in each line of data collected by the linear array (or TDI array), a correction factor which is the intensity level shown in FIG. 11. A better way to estimate the correction factor data set is to calculate the data set from several sequential data lines in a part of the image where there is no specimen (just a clear glass slide). Note that the correction for background fluorescence alone can be calculated by subtracting the dark-current noise floor value from each pixel value in the above diagram, which can be measured by scanning without a glass slide in the holder.

3) Correction of Crosstalk During Simultaneous Scanning of Multiple Fluorophores Measuring Two Fluorophores Simultaneously:

Suppose two fluorophores are excited simultaneously, red and green. A common problem is that the tail of the green fluorescence overlaps the red detection channel, causing the measured signal in the red channel to be increased by this overlap. This overlap can be reduced (or perhaps removed completely) by subtracting a fraction of the signal in the green channel from the signal in the red channel at each pixel position:

Measure the signal strength (intensity) in the green channel for each pixel in an entire scan line with only the green-exciting laser turned on. (Note: by green-exciting laser I mean whichever laser is exciting the fluorophore that emits in the green.)

Measure the signal strength in the red channel for each pixel in the same scan line with only the green-exciting laser turned on (this signal is crosstalk from the green fluorescence, plus maybe an offset signal from the dark current in the detector—more on this later).

Then, let Rg(i) [meaning Rgreen(i)] be the intensity measured by the red channel at pixel position i, where i varies from 0 to the last pixel in the scan line (9,999 for a scan line containing 10,000 pixels), caused by overlap of photons from the tail end of the green fluorescence spectrum onto the red detection channel, even when the laser that normally excites the red fluorophore is turned off Let Gm(i)=Gmeasured(i) be the intensity of the green fluorescence signal measured at each pixel in the same scan line, and Rm(i)=measured intensity of the pixels in the red channel when both lasers are turned on.

Then the corrected pixel intensities in the red channel are given by:

$$R(i)=Rm(i)-(Rg(i)/Rm(i))*Gm(i), \quad (2)$$

where the ratios Rg(i)/Rm(i) will have the same values for the 10,000 pixels in every scan line in the image.

Since the red fluorescence does not overlap the green channel, $$G(i)=Gm(i). \quad (3)$$

It probably makes sense to store the values of the overlap ratio (Rg(i)/Rm(i)) in a look-up table of 10,000 numbers (for a scan length of 10,000 pixels), since these ratios are the same for each scan line, assuming no changes are made in gain, laser intensity, scan speed or length, or alignment. For best calculation of the numbers to be stored in this table, they should be measured from a line scan when the green fluorescence is strong and nearly constant, and when preamplifier offset is set to compensate for dark current in the detector, or where the dark current level has already been subtracted from the detected signal. If the dark current correction has not been made before calculating the overlap ratio, the ratio calculated will depend on the dark current level as well as the overlap, and since the dark current level is constant for a particular exposure time (scan speed), the measured overlap ratios will depend on fluorescence intensity, and will be correct only for the intensity at which they were measured.

Where a strong uniform green fluorescence signal which is as long as the scan line is not available, it is possible to image an area of the specimen (TISSUEscope or other line-scan instrument) instead of collecting only a single line to calculate the overlap ratio. If an area containing N scan lines is imaged, with the green-exciting laser on, and with the mirror scan along the X direction and the stage scan along the Y direction, a pixel position is described as (i,j). Then $$Rg(i)/Rm(i)=\{\Sigma_{j=1\ to\ j=N}(Rg(i,j)/Rm(i,j))\}/N, \quad (4)$$

where the scan lines are numbered from j=1 to j=N.

Measuring three or more fluorophores simultaneously:

2) When three fluorophores are measured simultaneously, the situation is more complicated. When there are red, green and blue fluorophores, for example, it is probable that the tail of the blue fluorescence will add to measurements in the green channel, and the tail of the green fluorescence will add extra photons to the red detection channel. It is even possible that the leading (short wavelength) edges of a fluorescence spectrum will overlap the long-wavelength end of a detection channel for a shorter-wavelength fluorophore.

For this example, it is assumed that only the long wavelength tails of fluorescence spectra overlap the short-wavelength end of the next channel for a longer-wavelength fluorophore, and that red, green and blue fluorophores are used (other combinations are of course possible). Also, assume the blue-excitation laser excites a blue fluorescence that overlaps the green channel, but not the red channel. The green-excitation laser excites a green fluorescence that overlaps the red channel, as before.

The green channel overlap by the blue fluorescence is measured when only the blue-exciting laser is turned on, and the red channel overlap by the green fluorophore is measured when only the green-exciting laser is turned on.

Then:

$$B(i)=Bm(i) \quad (5)$$

$$G(i)=Gm(i)-(Gb(i)/Gm(i))*Bm(i) \quad (6)$$

$$R(i)=Rm(i)-(Rg(i)/Rm(i))*Gm(i), \quad (7)$$

Gb(i)/Gm(i) are ratios measured with only the blue laser turned on, and Rg(i)/Rm(i) are measured with only the green laser turned on. These ratios can be stored in a look-up table for efficient calculation in the computer, since the ratios do not change from one scan line to another.

If in addition to the overlap of long-wavelength tails as above, the leading (short wavelength) edge of the green and red fluorescence spectra overlaps with the blue and green detection channels, then:

$$B(i)=Bm(i)-(Bg(i)/Bm(i))*Gm(i) \qquad (8)$$

$$G(i)=Gm(i)-(Gb(i)/Gm(i))*Bm(i)-(Gr(i)/Gm(i))*Rm(i) \qquad (9)$$

$$R(i)=Rm(i)-(Rg(i)/Rm(i))*Gm(i) \qquad (10)$$

Where the ratios Bg(i)/Bm(i) and Rg(i)/Rm(i) are measured using a line scan (or image scan, as described above) with only the green laser turned on, Gb(i)/Gm(i) are measured with only the blue laser turned on, and Gr(i)/Gm(i) are measured with only the red laser turned on.

NOTE 1: Red, green and blue have been used as the colours of the fluorophores and detection channels in these examples. Any combination of colours (or wavelength ranges) can be used, and the number of fluorophores and/or detection channels is not limited to three. When there are four or more channels, the calculations are a simple extension of those given above.

NOTE 2: It is important to perform this overlap correction on the data from each linescan to preserve the relative position of the scanning laser spots, which are not usually perfectly coincident with each other, and whose relative positions may change slightly from one end of the scan line to the other. This means the overlap ratios will probably change along the length of the scan line, so using a single value for an overlap ratio for an entire scan line may result in poor correction of crosstalk.

NOTE 3: It is common to form a false colour image of fluorescence data by superimposing one fluorescence image over another, often with slight changes in relative pixel position to correct for the small differences in laser spot position along the length of the scan lines of different lasers (when multiple lasers are scanned, the scan lines are often slightly skewed from each other, and often do not start data collection at exactly the same position). If overlap correction is applied after these images have been superimposed, then the correction can produce ghost images because the correction should only be made between pixels that were illuminated simultaneously during the laser scan, and these pixels may not be at exactly the same pixel position in the final, superimposed image.

In a scanning-beam/scanning-stage microscope or macroscope, a sparse pixel image can be acquired in 1/10 of the time required for the final scan by increasing the speed of the scanning stage by a factor of 10, and only recording every tenth pixel in the beam scan direction. The sparse pixel image will contain only 1/100 of the number of pixels in the final image, but these pixels will have the same intensity and size as the same pixels will have in the final image. When the final image is very large, the scanning stage can be increased in speed by a factor of 100, and only one pixel in 100 recorded in the beam-scan direction. It has been found that sparse pixel images that are several (10-100) MPixels in size are very good predictors of the histograms of the final images. It has been found that this be true even for very large specimens where the final image file size will be more than 100 GB.

Figure 12:
FIG. 12 is a sparse pixel brightfield preview image of a stained tissue specimen. Pixel separation is 50 microns.
Figure 13:
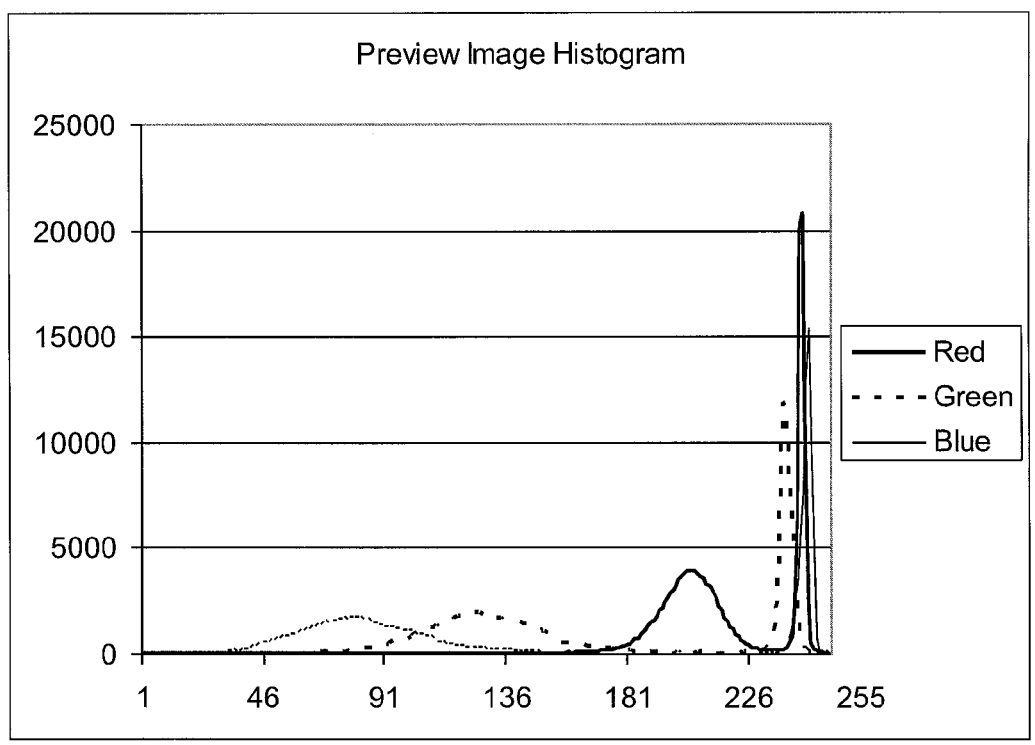
FIG. 13 is red, green and blue histograms calculated from the sparse pixel preview image shown in FIG. 12.

Brightfield Imaging:

When sparse pixel preview images are used in brightfield imaging, the Red, Green and Blue histograms of the sparse pixel image can be used to set the white balance before scanning the final image. FIG. 12 shows a 1.7 MB sparse pixel brightfield image of a stained tissue specimen on a microscope slide that is illuminated in transmission by red, green and blue lasers (other light sources could have been used). Scanning time for this sparse pixel image with 50 micron pixel separation was approximately 25 seconds. Red, green and blue histograms that describe this image are shown in FIG. 13. Note that the large peak on the right side of each histogram (the brightest pixels in the image) results from the laser beams being transmitted without absorption through the clear areas of the glass slide which are not covered by the tissue specimen. Since this area should be white (a combination of red, green and blue at maximum intensity), these peaks should coincide in the red, green and blue histograms. If the histograms calculated from the sparse pixel image are a true predictor of the histograms that will result after the final scan, then the white balance of the final image can be set by simply aligning these three peaks, and this can be accomplished on-the-fly when scanning the final image. For example, if the red peak had a maximum at level 250, and the green peak at 240, then all green pixel intensities are multiplied by 250/240 and the peaks will align. The blue peak can also be aligned with the red and green peaks using a similarly calculated multiplier, and the white balance adjustments made during acquisition of the final image data.

Figure 14:
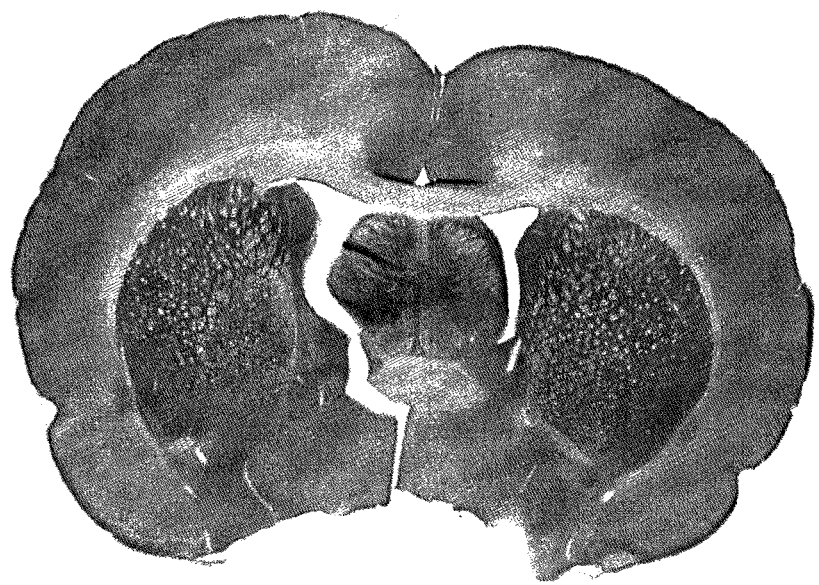
FIG. 14 is a final RGB image of the specimen shown in FIG. 12, with 1 micron pixels.
Figure 14:
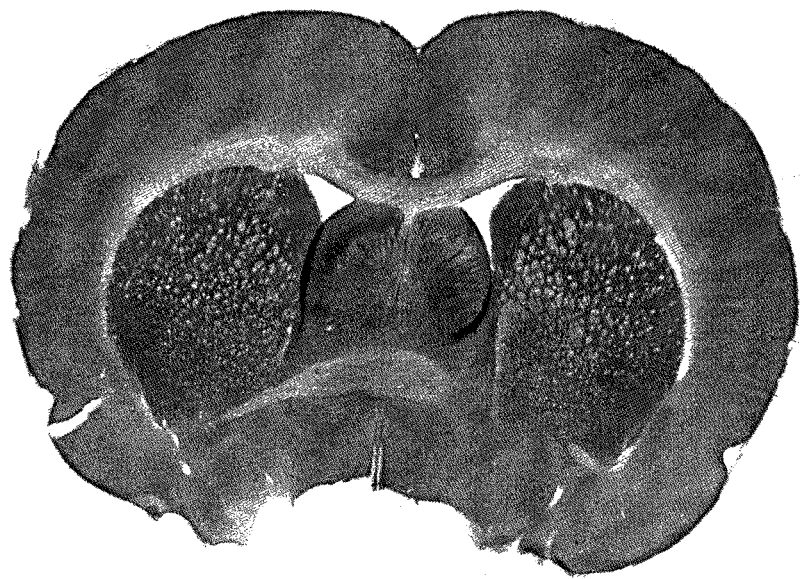
Figure 15:
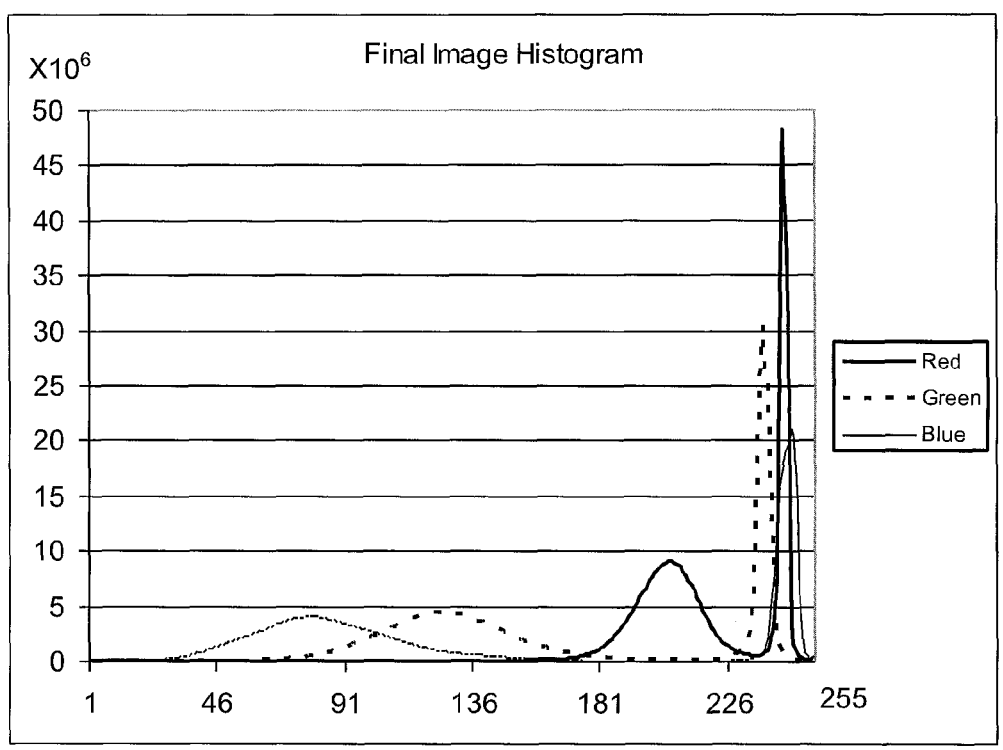
FIG. 15 is red, green and blue histograms calculated from the image in FIG. 14.

FIG. 14 shows the final image of this tissue specimen, scanned with 1 micron pixels. The file size is 1.18 GB, with a scan time of approximately 20 minutes. No adjustments were made to the instrument after scanning the sparse pixel image, and the histograms in FIG. 15 clearly show that the sparse pixel image histograms are good predictors of the final image histograms, and could have been used to calculate the multiplicative constants to correct white balance during scanning of the final image.

Figure 16:
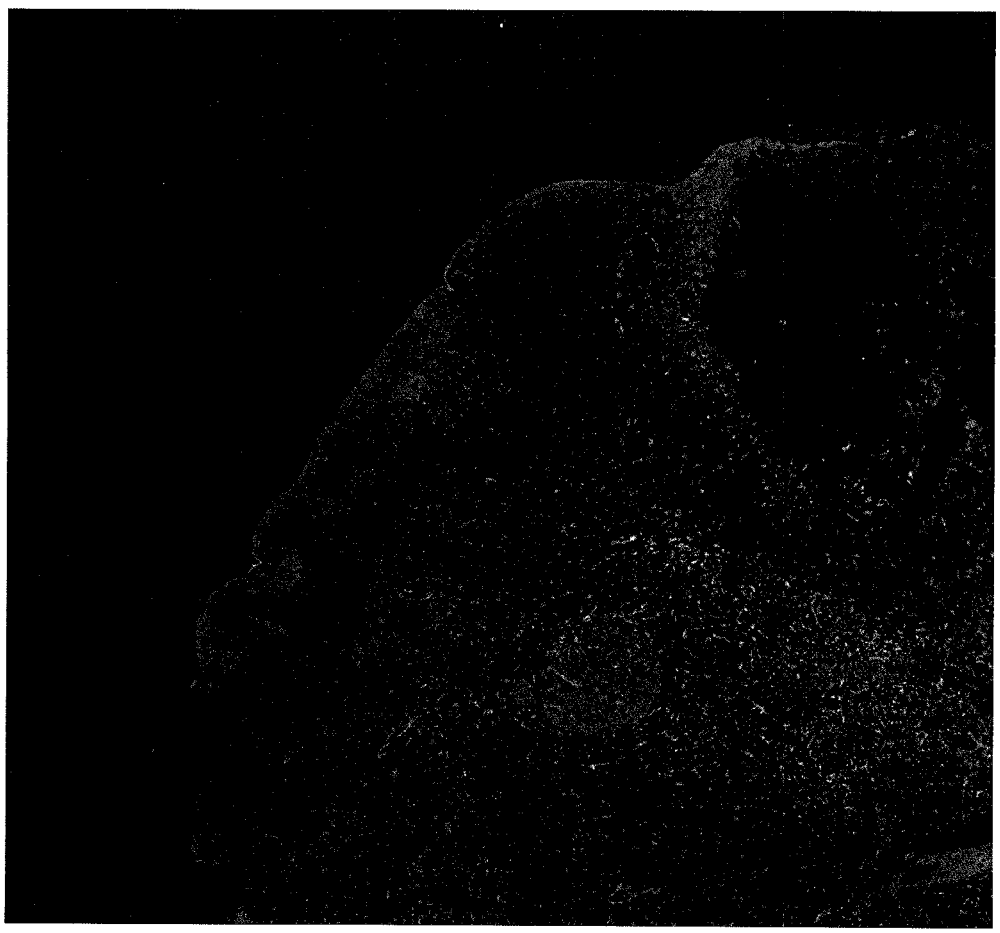
FIG. 16 is a fluorescence image of a small area of a tissue specimen. This 12-bit image was converted directly to 8 bits.
Figure 17:
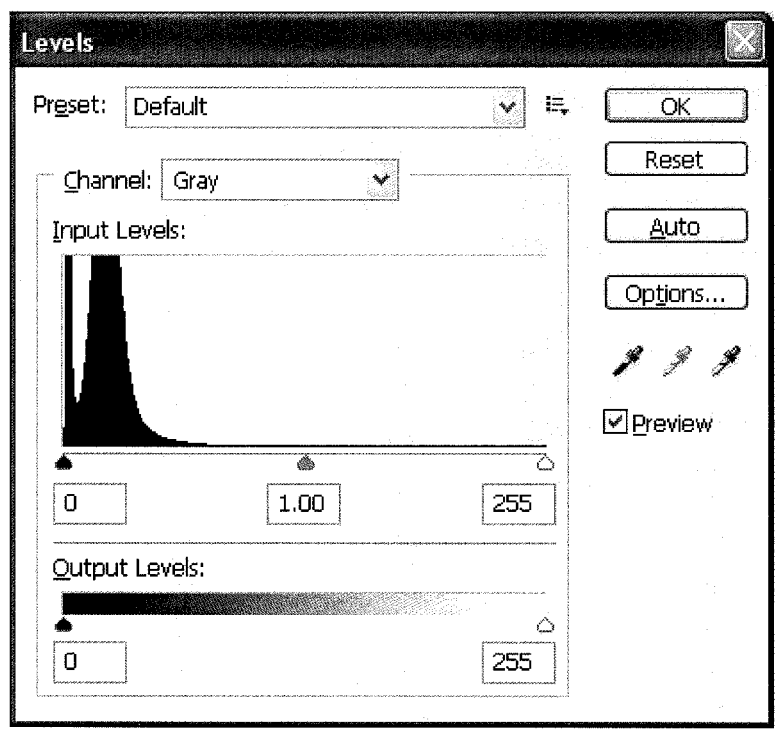
FIG. 17 is a histogram of the image in FIG. 16, calculated in Photoshop.

Fluorescence Imaging:

FIG. 16 shows a fluorescence image of a small area of a large tissue specimen. This image was scanned using 12-bit detection, and displayed as an 8-bit image by simply dividing the intensity value of each pixel by 16. The resulting image is almost entirely black, with very poor contrast. The histogram of this image in FIG. 17 shows the problem—a high narrow peak on the left side of the histogram (the black end of the histogram) is comprised of a large number of very dark pixels in the area of the microscope slide where there is no tissue, and the fluorescence signals from the tissue are in the broad peak just to the right of the narrow peak. By simply dividing by 16, the information from the tissue fluorescence has been concentrated into a peak that is less than 70 levels wide, or approximately 6 bits in dynamic range.

Figure 18:
FIG. 18 is an image based on the same 12-bit data file as used for FIG. 16, however contracted to 8 bits so that the dynamic range of the fluorescence data in the 12 bit file is preserved.
Figure 19:
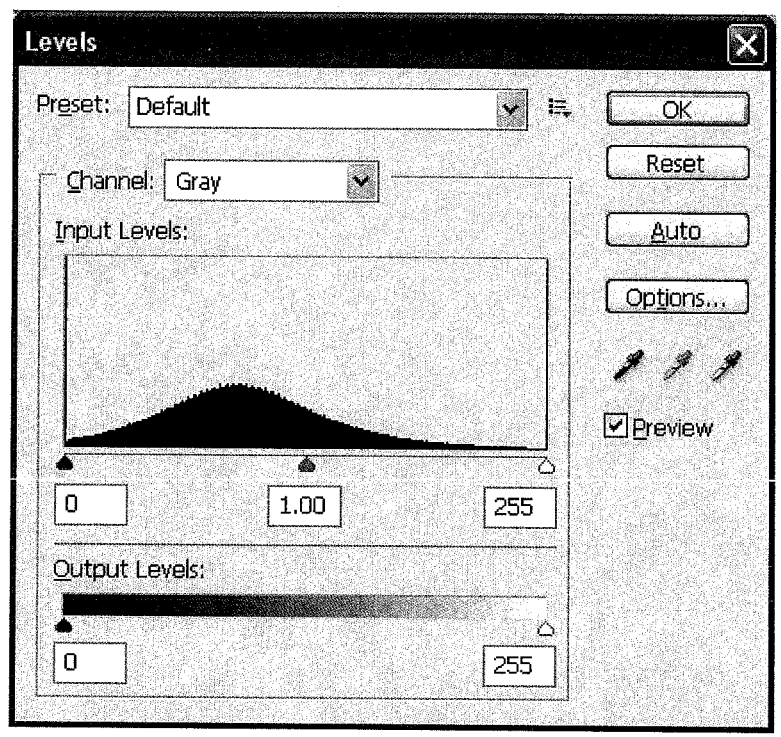
FIG. 19 is a histogram of FIG. 18 showing the dynamic range of fluorescence information in the original 12-bit file has been conserved in the image of FIG. 18.

To properly display the fluorescence information in the broad peak, the original 12-bit image should have been contracted to 8 bits by expanding the data inside the broad peak to fill the entire 8-bit range of the output file. This technique is described in detail later in this document, along with the description of FIG. 23. When properly contracted, the resulting image is shown in FIG. 18, and the contracted histogram is shown in FIG. 19. The resulting image shows a large amount of detail that was missing in FIG. 16. In the histogram of FIG. 19, there is a very large peak at 0 which comprises all of the pixels on the left side of the broad peak in FIG. 17 (they are all now black) and a smaller narrow peak at 255 which comprises all of the pixels that were brighter than those in the broad peak (a relatively small number), which are now white.

Figure 20A:
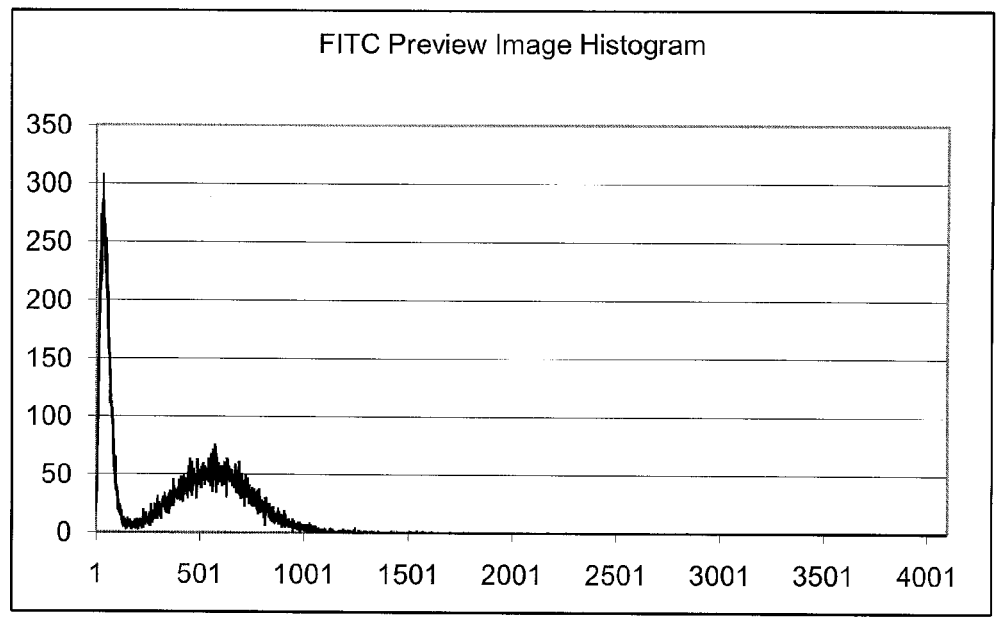
FIG. 20 is a preview image and final image histograms for the FITC fluorescence channel from the specimen imaged in FIG. 16, showing that the sparse preview image histogram correctly predicted the characteristics of the final image histogram.
Figure 20B:
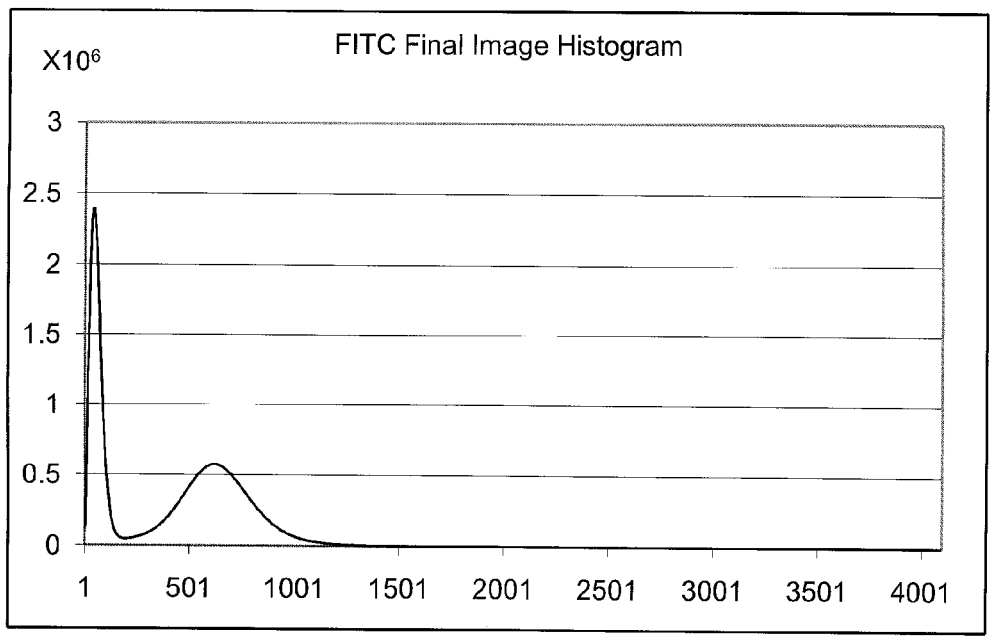
Figure 21A:
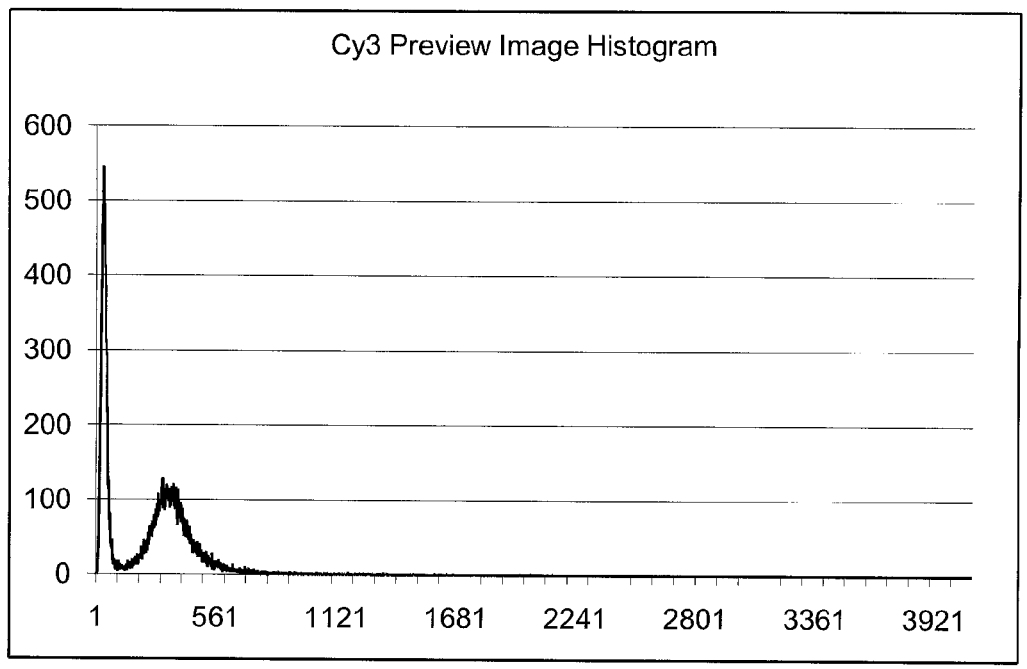
FIG. 21 is a preview image and final image histograms for the Cy3 fluorescence channel from the specimen imaged in FIG. 16, showing that the sparse preview image histogram correctly predicted the characteristics of the final image histogram.
Figure 21B:
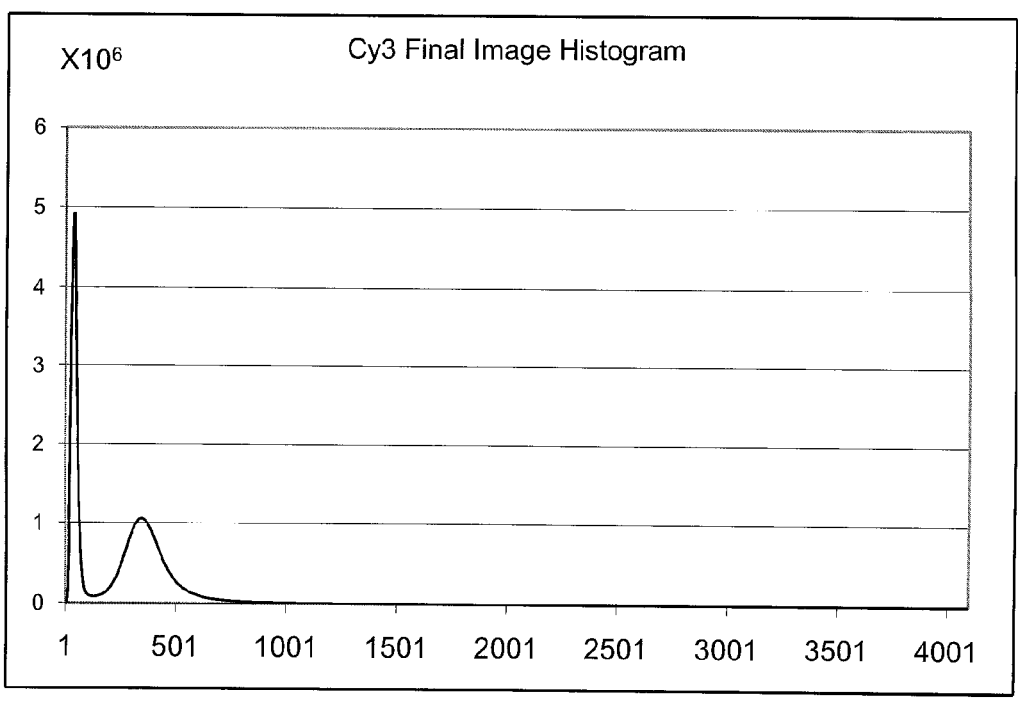

The tissue specimen shown in FIG. 18 contains two fluorophores, Cy3 and FITC. In order to show that the histogram calculated using a sparse pixel preview image correctly predicts the histogram of the final image, sparse pixel and final images were acquired for both fluorophores, and histograms were calculated for all four images. FIG. 20 shows the preview and final image histograms for FITC, and FIG. 21 shows the preview and final image histograms for Cy3. In both cases, the sparse pixel preview images correctly predicted the final-image histograms, even though the preview images were only 82 KB in size, while the final images were 132 MB. The dynamic range of the FITC data is slightly larger than that of Cy3. The dynamic range of the data from a fluorophore can be increased by increasing fluorescence exposure, or by increasing the gain in the detection channel. If the output file required is a 12-bit file, then the gain should be increased until the tail of the fluorescence peak on the right side is beyond 2048 (if gain is increased by factors of two) or as close to 4096 as possible. On the other hand, if the required output is an 8-bit file, there are more than 256 levels in each of the broad peaks in FIGS. 20 and 21, so no further gain adjustment is necessary to produce an output file that fills the entire 8-bit dynamic range.

1) As stated earlier in this document, one of the most difficult parts of fluorescence imaging, especially when imaging multiple fluorophores simultaneously, is setting the gain (exposure) and offset (to remove dark current noise) on each detection channel to maximize the measured dynamic range for each fluorophore, without saturating some pixels and/or using an offset voltage that is larger than that required to just offset the dark current noise floor.

Figure 22:
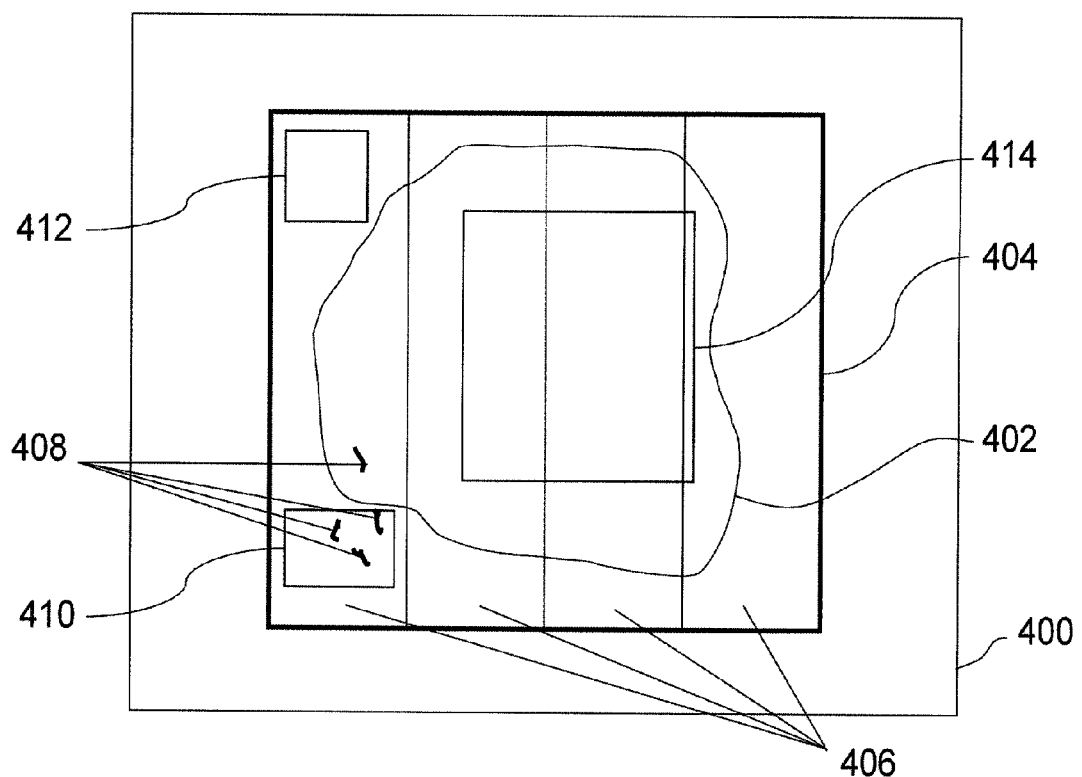
FIG. 22 shows a specimen and various scan areas inside the area of a large microscope slide.

FIG. 22 shows a tissue specimen 402 mounted on a large microscope slide 400. This example illustrates a large 5×7 inch microscope slide and a very large tissue specimen, however any size microscope slide and tissue specimen can be used. A preview scan area 404 (which has the same area as the cover slip) was used to find the area occupied by specimen 402. The preview scan shown is comprised of four scan strips 406. A histogram of the preview scan image will include pixels from inside the specimen area 402 (which can be used to estimate the range of signals that will come from fluorescence in the tissue specimen) and from areas of the microscope slide that does not contain specimen (which will estimate the signal strength from dark current noise and fluorescence background from the glass). This figure also illustrates the possible existence of bright fluorescent dust particles 408, which should be taken into account when setting the gain of the system (since in most cases it doesn't matter whether the pixels representing the dust are saturated). In addition, the figure shows an area 412 inside the cover slip that can be scanned to produce a histogram to estimate the fluorescence background signal from the glass slide, an area 414 that is completely inside the area of the specimen that can be scanned to produce a histogram to predict the gain settings for imaging the specimen, and an area 410 that contains only dust particles. The histograms from preview scans (or even full resolution scans of these or smaller versions of these areas) can be used to direct gain and offset adjustments for the instrument before scanning the entire tissue area at high resolution.

A first embodiment of this invention is a method and macroscope that will:

image the entire specimen rapidly in preview mode, where only a small fraction of pixels (a sparse image) are recorded across a field-of-view that includes the entire specimen, where those pixels have the same size and exposure as those same pixels would have in the final image if no changes were made in detection gain and offset before scanning, Calculate and display a histogram of the preview image, Increase (or reduce) the detection channel gain so that the brightest pixel in the preview image has a value less than the maximum pixel value for the dynamic range of the detection system, Adjust the preamplifier offset (if possible) to move the dimmest pixel in the preview image close to the 0 end of the histogram.

Figure 24:
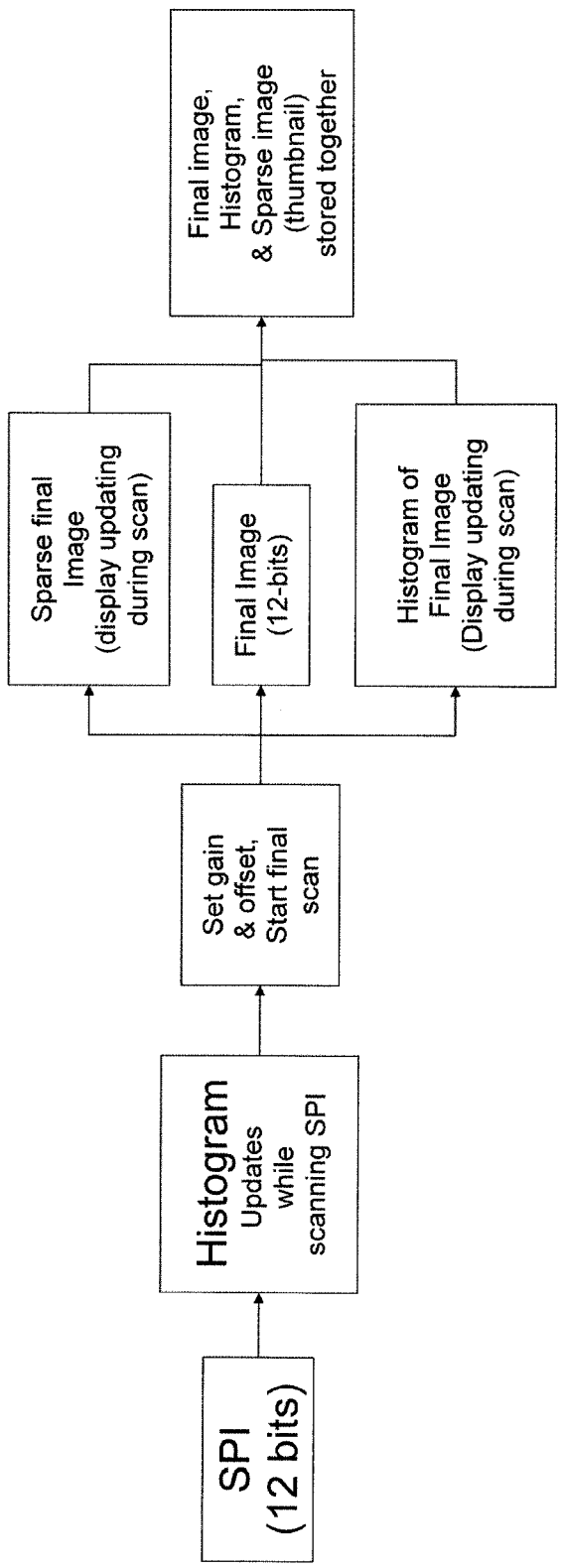
FIG. 24 is a histogram of sparse preview image guides instrument set-up for scanning. Final Image with Sparse Final Image and Final Image Histogram are calculated on-the-fly during scan.

FIG. 24 shows the series of steps for imaging in which a histogram of the Sparse Preview Image (a separate histogram for each fluorophore or channel) is used to set gain and offset for each channel, and during scanning a new histogram and sparse final image are calculated on a line-by-line basis and stored with the final image file.

As an example, if the specimen is to be scanned with 1 micron pixels, a preview image with sparse pixels spaced 10 microns apart will contain only $\frac{1}{100}$ as many pixels and this scan can be accomplished 10 times faster than the final 1 micron scan. It is important that the pixel size be the same in both the preview image and in the final image; otherwise there will not be a linear relationship between the pixel values (fluorescence intensities) in the preview image and those in the final image. For example, if a preview image were made using a lower-power objective (as would normally be done in a tiling microscope), the pixels will be larger (cover a larger area of the specimen) and each pixel would average the intensities of the small features that exist inside the area represented by the larger pixel. This is particularly important where small features (like quantum dots) are imaged in fluorescence, because larger pixels in the preview image will underestimate their fluorescence intensity. On the other hand, a preview image with sparse pixels may miss them entirely, so care must be taken when there are only a few small bright objects in the specimen.

NOTE: If the specimen is very large and has uniform fluorescence, it may be possible to predict the gain and offset settings using a preview scan of a smaller area than that of the entire specimen; however this smaller area should be chosen to include both bright and dim areas.

NOTE: If a spectrally-resolved detection arm is used, for example containing a spectrometer and multi-anode pmt or other linear array detector, the channel containing the largest signal should be used for estimating the largest data value to preserve relative intensity between channels.

2) When imaging multiple fluorophores, the procedure is as above, except that each fluorophore and detection channel is handled separately, with a separate histogram for each channel.

3) When very large specimens are imaged, the image data files are huge, and one way to reduce the size of these files is to use 8-bit data instead of 12-bit or 16-bit data. Since there are only 256 different levels in an 8-bit file (it's dynamic range), it is important to use as many of these levels as possible.

A second embodiment of this invention is a microscope (or slide scanner) that has a larger dynamic range for measurement than the dynamic range required in the final image, and a method for contracting the dynamic range of the measured data to use all or substantially all of the dynamic range available in the final image file. (The image shown in FIG. 5 is a good example of an image where the gain and offset were incorrect, and only part of the dynamic range of the final image file was utilized.)

Figure 23:
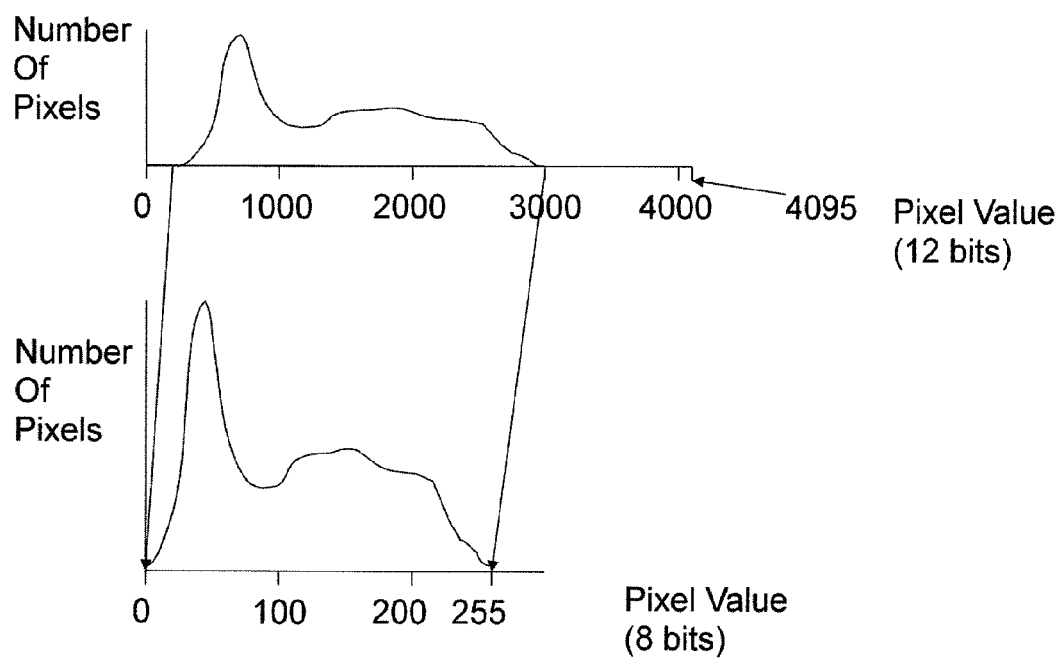
FIG. 23 is a histogram for a 12-bit image (top) guides contraction of the image data to fill the dynamic range of the final output 8-bit image (histogram at bottom)

One example of such an instrument is a macroscope with a dynamic range of 12 bits per channel, where the dynamic range required in the final image file is 8 bits per fluorophore (each fluorophore is imaged using a separate channel). A histogram of hypothetical fluorescence image data from one 12-bit channel of the macroscope is shown at the top of FIG. 23, which shows a plot of the Number of Pixels (vertical axis) vs. Pixel Value (fluorescence intensity) on the horizontal axis. This plot shows the number of pixels in the image that have a particular pixel value (or fluorescence intensity). Note that in this example there are no pixels with a pixel value below approximately 200 (this is the noise floor, the magnitude of which depends on pmt gain, offset and exposure time), so the first real fluorescence data starts at level 200. Also note that the largest pixel value is at approximately 3000, which is the value for the brightest pixel in the image. If the gain of the instrument were increased by a factor of two, that would cause any pixels with values greater than 2047 on this diagram to saturate, which would result in a sharp peak in the diagram at 4095, indicating saturated pixels and that the gain should not have been increased by a factor of two. Since one of the important measurements in fluorescence imaging is relative fluorescence intensity across the specimen, saturated pixels would make this comparison impossible.

A 12-bit image whose histogram includes levels below the noise floor with substantially zero number of pixels, and levels above the brightest pixel in the image with substantially zero number of pixels, can be contracted into an 8-bit dynamic range while preserving the relative intensity of the fluorescence signal and using substantially all of the 8-bit dynamic range available in the final image file. (The term "substantially zero number of pixels" is used because there may be a few very bright pixels caused by fluorescence from dust on the slide, or other fluorescence, that should be ignored in the contraction process.) If field flattening corrections or fluorescence background corrections are to be performed, they should be performed before dynamic range contraction, and the histogram should be re-calculated to represent the data after field flattening and fluorescence background subtraction but before dynamic range contraction.

The contracted image histogram is shown at the bottom of FIG. 23. Dynamic range contraction is performed by first subtracting the lowest Pixel Value (200 in this example) from each pixel, and then linearly distributing the remaining pixels, which have a range of approximately 2800 levels in brightness in this example, over the 256 different levels (Pixel Values) in the final 8-bit data file. The result will be an output image data file with 8-bit dynamic range in which substantially all of the 256 levels are used.

Mathematically, this dynamic range contraction operation can be described as follows (where PV stands for Pixel Value):

For each pixel in the image, from n=1 to n=the number of pixels in the image, $$PV_n(\text{8-bits}) = \{[PV_n(\text{12-bits}) - PV_{min}(\text{12-bits})]/[PV_{max}(\text{12-bits}) - PV_{min}(\text{12-bits})]\} * 255 \quad (11)$$

So the dimmest pixel in the 12-bit image (Pixel Value=200 in this example) has the 8-bit value $PV=\{(200-200)43000-200)\}*255=0$, and the brightest pixel in the 12-bit image (Pixel Value=3000 in this example) has the 8-bit value $PV=\{(3000-200)/(3000-200)\}*255=255$.

NOTE: This dynamic range contraction can be applied to each strip of a multi-strip image, but must be based on the histogram from the entire image, not just one strip, otherwise the contraction will not be uniform across the entire image.

NOTE: If dynamic range contraction is done such that (at least) one pixel value at the bottom and one at the top of the range (PV 0 and PV 255) are empty, it will be clear from the contracted image histogram that no pixels exist in the uncontracted image from below or above the range of pixel values that were chosen for contraction, so there are no saturated pixels or pixels below the chosen minimum value in the uncontracted image. In this circumstance, the formulas change so that the dimmest pixel (Pixel Value=200 in this example) in the 12-bit image has an 8-bit value given by $PV=\{(200-200)/(3000-200)\}*253+1=1$, and the brightest pixel in the 12-bit image (Pixel Value=3000 in this example) has the 8-bit value $PV=\{(3000-200)/(3000-200)\}*253+1=254$. This leaves the levels 0 and 255 empty showing that there were no pixels in the uncontracted image below or above the chosen pixel value range.

4. It is important to provide the user with as much information as possible about the image file that has been collected. It has become common to attach information about instrument settings, a description of the specimen, the operator's name, date, etc. to the file as metadata. Often a researcher wants to apply an image analysis algorithm that is specific to his research needs to the image data file. A histogram of the image data in the file is usually required and because of the large image file sizes generated when large specimens are scanned at high resolution, opening the file to calculate and display this histogram may take as long as it did to image the specimen in the first place.

A third embodiment of this invention is to provide a microscope (or slide scanner) and method for calculating, displaying and storing as metadata attached to the final image file a histogram of the pixel intensity data in that image file, where the histogram is calculated on-the-fly during scanning. A separate histogram is required for each fluorophore.

When using a 12-bit detector, 4096 memory locations are dedicated to storing the histogram. The TISSUEscope will be used as an example. During scan, data from each fluorophore scan line is transmitted from the TISSUEscope optics module to the computer controlling the scan. These scan lines usually contain from 10,000 to 40,000 data points (pixels) which are used to update the image display on the computer screen and are stored in a data file in RAM (for small image files) or on a hard drive or other storage device (for large image files). To calculate an image data histogram on-the-fly, during scan, the pixel value of each data point in that scan line (pixel position in the specimen) is compared with the pixel value that describes each of the 4096 memory locations representing the 12-bit range, and when a match is found, the number stored in that memory location is increased by 1. The histogram can be displayed during scanning as it is being updated along with a sparse image showing the scan in progress. At the end of the scan, the histogram is stored as metadata inside (or attached to) the image file. The sparse image can be saved as well. When multiple fluorophores are imaged and stored in the same file, a separate histogram (and sparse image) is stored for each fluorophore. For example, when three fluorophores are displayed in false colours where red, green and blue represent the three fluorophores, it is common to store the image as a 24-bit RGB image. In this case, one histogram and/or one sparse image for each of the three false colours (representing the three fluorophores) are stored with the image as metadata.

5) For some applications, the entire image histogram is not required, and the only information needed is the pixel value of the brightest pixel in the image. If this value is equal to 4095 in a 12-bit image, this immediately tells the operator that one or more pixels are saturated. For instruments where the dark current noise floor is low, or an offset has been applied to the preamplifier to minimize the dark current signal, a simplified version of dynamic range contraction can take place without using the dark-current noise floor value. This can be accomplished by storing the value of the brightest pixel in a single memory location: during scanning, the intensity value for each pixel is compared with the value already stored in that memory location (starting from a stored value of 0), and if the pixel value is larger than the number stored, the stored number is replaced by that pixel value. At the end of the scan, this location contains the value of the brightest pixel in the image, which can be used for simplified data contraction where PVn (12-bits)=0 in Formula (11).

6) It is an object of this invention to provide a method of using the data stored in the image histogram that is measured and constructed during scan to contract the dynamic range of the image data file after the scan is complete, and to provide a method of performing such contraction to start automatically (or manually initiate start of the operation at some later time) on the stored image data files of scan strips before the final image is assembled, and in such a way that this operation can be performed in the background while the next scan is underway.

It is a fourth embodiment of this invention to provide a macroscope (or slide scanner) and method for calculating, displaying and storing as metadata attached to the image file a histogram of the pixel intensity data in the image file, where the histogram is calculated on-the-fly during scanning, and when scan is complete (and the histogram is completed), automatically performing a dynamic range contraction of the file. This dynamic range contraction operation can proceed in the background after the scan is complete, by loading data from the intermediate 12-bit image data file into RAM one-scan-line-at-a-time, and performing the data contraction as described earlier. After dynamic range contraction, the data is stored one-scan-line-at-a-time in a contracted image file with smaller dynamic range (this is the "output image file" or "final image file"). When using a computer system with multiple cores, one core can be dedicated to this task, which can be performed in the background while the instrument is scanning a new specimen. If the intermediate 12-bit image file is stored on a hard drive, it may be faster to read from that hard drive and write the contracted file to a second hard drive to avoid multiple read-write operations on the same drive.

Figure 26:
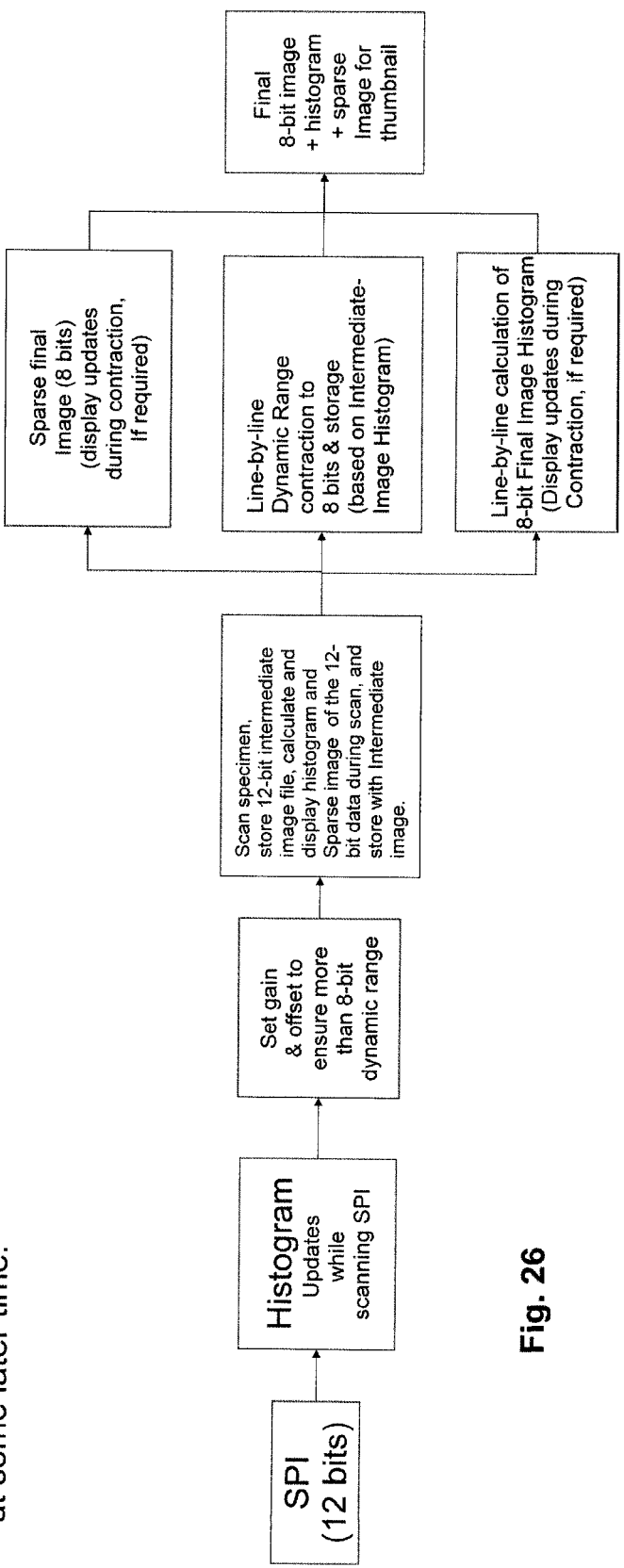
FIG. 26 is a Dynamic Range Maximization using a detector that has a larger dynamic range than required in the final image file. In this case an intermediate image is produced with the same dynamic range as the preview image, and the data histogram of the intermediate image is used to direct dynamic range contraction to produce the final image file.

FIG. 26 shows Dynamic Range Maximization using a detector that has a larger dynamic range than required in the final image file (in this example, a 12-bit detector is used when an 8-bit final image is required). The Histogram of a12-bit Sparse Preview Image guides instrument set-up for scanning and storage of a 12-bit intermediate image, histogram and sparse image. At a later time, scan data from the intermediate image is loaded back into RAM on a line-by-line basis, and the 12-bit intermediate image histogram guides contraction to an 8-bit Final Image with Sparse Final Image and Final Image Histogram. Contraction of the Intermediate image can take place as a background task during the next scan or at some later time.

7) It is an object of this invention to provide a method of using the data stored in the preview image histogram to automatically contract the dynamic range of the image data file while the scan is underway ("on-the-fly).

It is a fifth embodiment of this invention to provide a macroscope (or slide scanner) and method for automatically performing a dynamic range contraction of the scanned image data on-the-fly, using the preview scan histogram or data obtained from small-area scans to direct the dynamic range contraction process, at the same time calculating a new histogram that describes the data in the contracted file, and saving the contracted file with the new histogram included as metadata. A sparse image based on the contracted file can also be saved as metadata.

Figure 25:
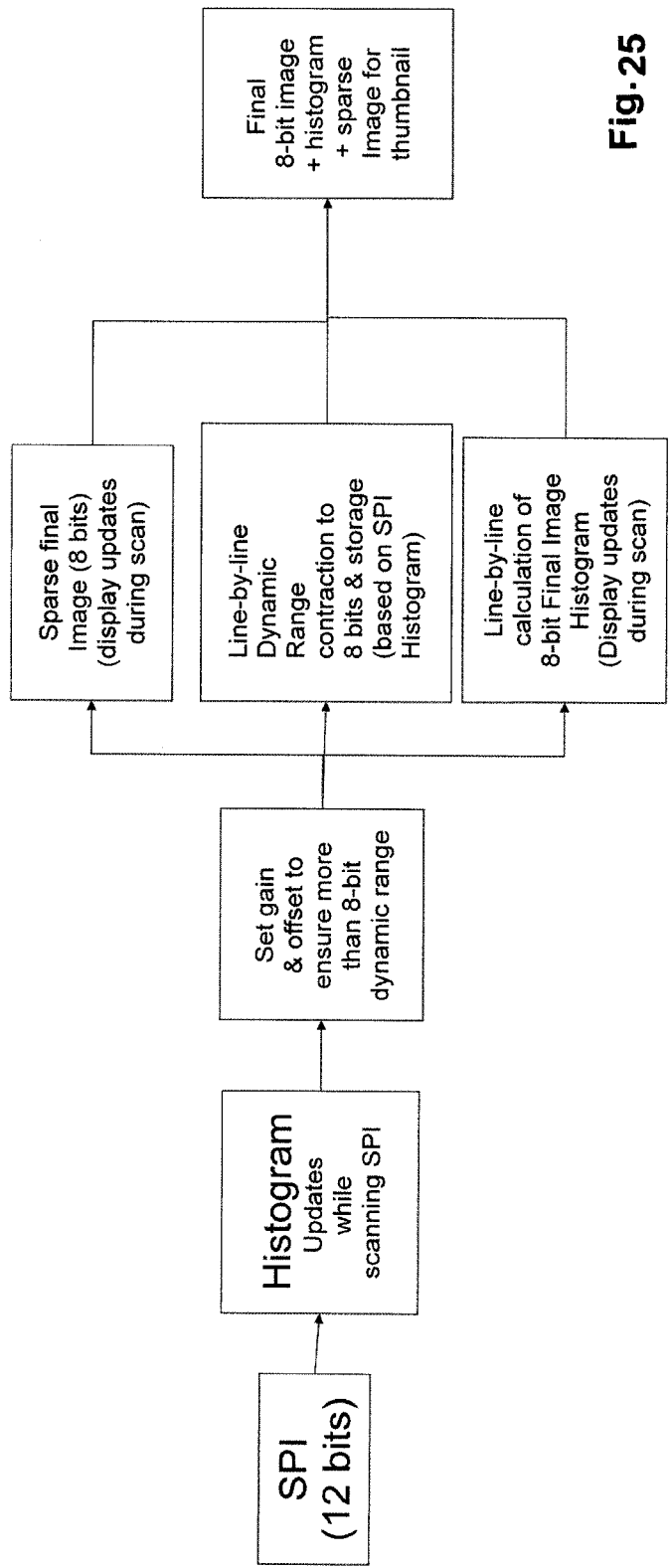
FIG. 25 is a Dynamic Range Maximization using a detector that has a larger dynamic range than required in the final image file.

FIG. 25 shows the steps required to scan a specimen using the histogram of the Sparse Preview Image to set gain and offset for each channel, then perform line-by-line contraction to a smaller dynamic range and at the same time calculate a sparse final image and histogram of the final image. The final image is stored line-by-line during contraction, with the final image histogram and sparse final image added later as metadata.

8) It is an object of this invention to provide a method of performing a series of data processing steps during scanning that will automatically correct for one or more instrument properties, including but not limited to dark current noise floor correction, flat field correction, correction for background fluorescence from the glass slide, correction for overlap between adjacent fluorescence channels, and image dynamic range contraction. If image dynamic range contraction is required, the instrument must have a larger dynamic range for detection than that required in the final output file.

The preferred (sixth) embodiment of this invention is an instrument for and method of performing a series of data processing steps during scanning that in addition to dynamic range contraction will also correct for one or more instrument properties, including but not limited to dark current noise floor correction, flat field correction, correction for background fluorescence from the glass slide, and correction for overlap between adjacent fluorescence channels.

Since this instrument and method acts automatically on the data during scan, it must rely on calibration data obtained before the scan starts. Some of this data is instrument-specific (and can be obtained through instrument calibration from time to time), some is specific to the specimen being imaged (and can be obtained from a preview scan of the image), and some may require full-resolution scans of small image strips before the final image data scan starts.

The instrument-specific data includes flat-field correction data that is measured by imaging a uniformly-fluorescent test sample for each combination of excitation laser, filter set and detection arm, as described earlier in this document. This sample should have uniform fluorescence along the entire length of the scan line. Dark-current noise floor can be measured (for each detection arm/laser/filter set combination) by scanning with the microscope slide removed. These instrument-related measurements can be performed from time to time, or when the combination of laser, filter set and detection channel is changed. Measurement of overlap between fluorescence channels should also be completed before imaging following the instructions earlier in this document.

Measurement of background fluorescence from the glass slide should be performed whenever the type of glass slide is changed. In order to include background fluorescence from the cover slip and mounting medium, it makes sense to make these measurements inside the area covered by the cover glass, but outside the specimen itself.

A preview scan of the specimen is used to generate a preview-image histogram for each fluorescence channel. This histogram is used to direct the dynamic-range contraction of the image during scanning.

Changes to the data will be made on a line-by-line basis, and before storage of each line the final image histogram is updated, so that the image histogram stored with the final image file is the correct histogram for data in that file (or the correct histograms if more than one fluorophore is used).

Assuming the instrument calibration steps have been performed at an earlier time, the steps for imaging the specimen are as follows:

1. Load the microscope slide containing the specimen into the macroscope.

2. Input which fluorophores are in use (the instrument chooses the correct laser, filter set and detector combination for each).
3. Choose which instrument properties are to be corrected for on-the-fly.
4. Perform a preview scan of the slide to find the area containing the specimen.
5. After selecting the area to be imaged, mark the positions on the preview scan for auto focus and tilt measurements, and perform auto focus and tilt to define the specimen plane to be imaged.
6. If required, adjust the gain and offset of one or more fluorescence channels. If any changes are made in this step, a new preview scan will be required (or if these adjustments are made in calibrated steps, the original preview histogram can be automatically adjusted to reflect these changes.
7. Start the scan. As each line of data is acquired (for each fluorophore), the computer performs data corrections on a pixel-by-pixel basis. Data correction can be performed in the following order:
    Apply field flattening correction to the line (if required).
    Apply crosstalk correction between channels (for multiple fluorophores, if required)
    Apply Data Contraction algorithm:
        a. Subtract the dark current noise and background fluorescence level from each pixel in the line (depends on pmt gain and preamplifier offset and gain for each detection channel).
        b. Adjust preview scan histogram by subtracting the dark current level number from each pixel level number (shifts histogram to the left a distance equal to the dark current level).
        c. Linearly distribute all pixels so the filled levels in the adjusted preview scan histogram are distributed to fill the 256 levels in the 8-bit output file.
        i. b. and c. are accomplished using Formula (2).
        d. Calculate a new histogram for the 8-bit file as the 8-bit data is stored on a line-by-line basis.
        e. Store pixel values for pixels in a new sparse image that will replace the preview image.
        f. Store the completed histogram as metadata with the 8-bit data file.
        g. Store the new sparse image that represents the 8-bit image data file with that file as metadata.
9) It is an object of this invention to provide a means and method for fluorescence imaging of microarrays in which the correct gain setting and dark current offset can be estimated from a preview scan of the entire specimen (a sparse preview image) or part of the specimen, and perform dynamic range contraction automatically during scan. A histogram of the output image data file can be prepared automatically during scan and saved as metadata with the output image data file if desired.

Most scanners for imaging genetic or protein microarrays use 16-bit dynamic range detectors to produce a 16-bit dynamic range output image file. The dynamic range of fluorescence data from microarrays can be very large (sometimes larger than 16 bits) and in addition there is often a background fluorescence from the glass microscope slide in addition to dark current noise that increases with instrument gain. With 16-bit detectors it is very difficult to set the offset and gain for proper exposure. A small increase in gain can cause some pixels to saturate, resulting in incorrect fluorescence intensity for the microarray features with saturated pixels. On the other hand, 16-bit data files are the standard in microarray analysis, and are required by most analysis programs.

It is a seventh embodiment of this invention to provide a means and method for scanning microarrays using a detector dynamic range that is larger than that required in the output data file, automatically performing a dynamic range contraction of the scanned image data on-the-fly, using the preview scan histogram or data obtained from small-area scans to direct the dynamic range contraction process, at the same time calculating a new histogram that describes the data in the contracted file, and saving the contracted file with the new histogram included as metadata.

For example, if a microarray scanner uses an 18-bit dynamic range detector, the data has 262,144 unique values. If a 16-bit output data file is required, which has 65,536 values, the gain and offset of the scanner should be set such that the range of data in the 18-bit file is larger than 65,536 (a good target is between 100,000 and 200,000), so that dynamic range contraction can be used to remove dark current noise, fluorescence background from the glass slide (or other substrate), and crosstalk between channels, and the final result is a 16-bit output file that uses substantially all of the 16-bit dynamic range. Initial settings of gain and offset can be made as before, using a preview image, or by using settings that have worked well in previous microarrays from the same batch.

It is an eighth embodiment of this invention to provide a method and means for contracting the data measured by a scanner to fill the dynamic range of the output image file, where such contraction is directed by the brightness of two fluorescence calibration markers on or embedded in the specimen holder (most commonly a microscope slide). One example is a genetic microarray in which a dilution series is spotted on the slide such that the fluorescence intensity in the series is unchanged by the subsequent actions of the user during his experiment or test. If the image contraction is made between the intensity values of a bright spot in the series and a dim spot, the final output file will span the dynamic range between these two calibration spots, and this will automatically correct for differences in sensitivity between scanners. For the simplest application, two fluorescent calibration features, one bright and one dim, can be used for each fluorophore. This will be particularly important for diagnostic purposes, where it is important that there be no variability between instruments.

Figure 27:
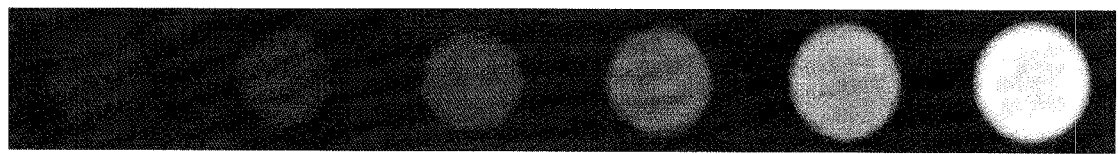
FIG. 27 is a dilution series from a genetic micro array calibration test slide.
Figure 28:
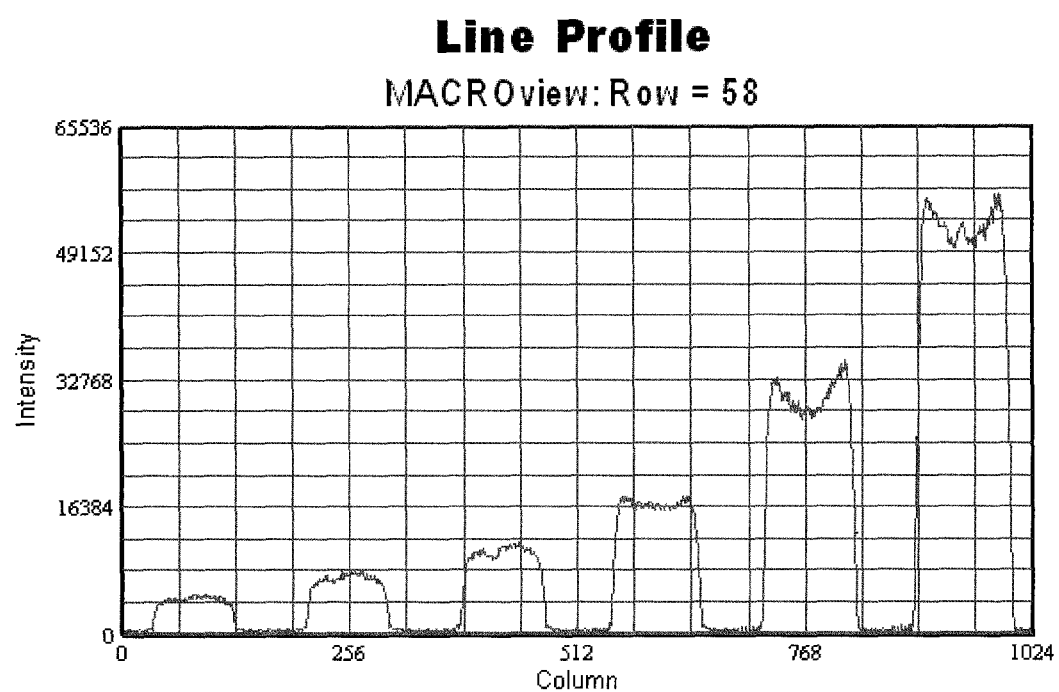
FIG. 28 is a line profile of intensities across the image of the dilution series shown in FIG. 27.
Figure 29:
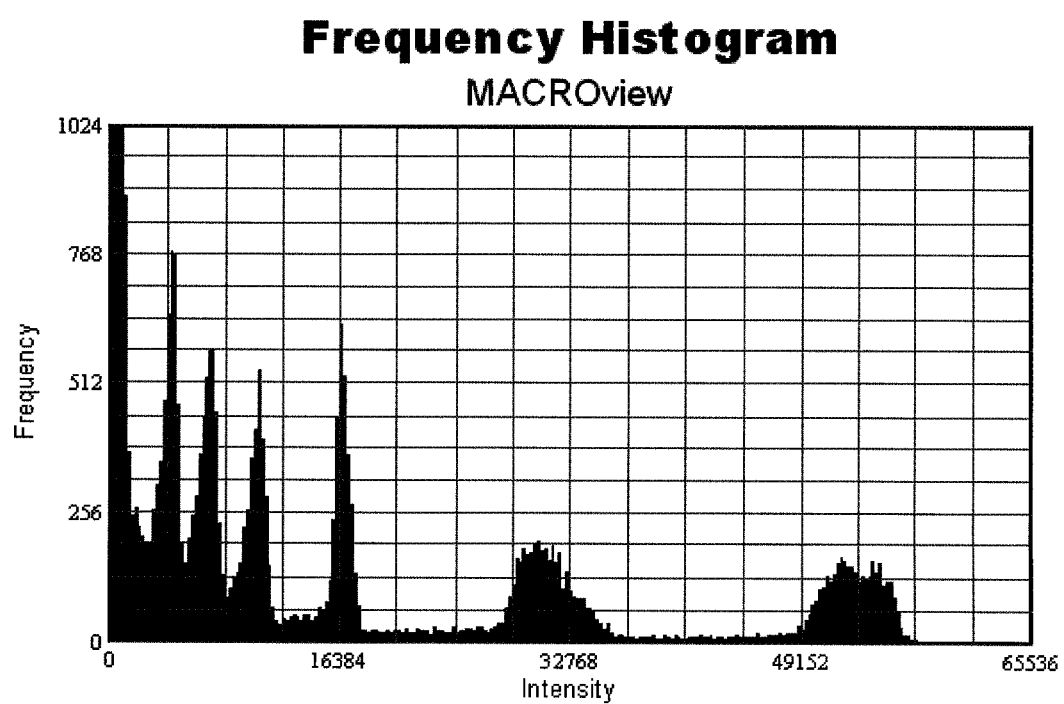
FIG. 29 is a histogram of the image shown in FIG. 27.

FIG. 27 shows an image of a fluorescence dilution series from a genetic microarray, and FIG. 28 shows the intensity range from a single linescan across the dilution series. FIG. 29 shows a histogram of the image in FIG. 27.

FIG. 29 a histogram of FIG. 27.

Either the Line Profile of FIG. 28 or this histogram can be used to define the range of intensities to be used in the output file for dynamic range contraction. All six features in the dilution series are clearly seen above the noise floor.

NOTE: Many of the operations and methods described in this patent document apply to other slide scanners in addition to those based on the scanning laser macroscope, and these operations and methods are included in this description. LED's or other monochromatic or broadband light sources can be used in place of lasers.

I claim:

1. A method of operating a macroscope to image an entire specimen rapidly in a preview mode, said method comprising having a detector record intensity values for only a small fraction of single pixels equally spaced across a field of view that includes the entire specimen, said fraction being single pixels that are equally spaced from one another and that have the same size and exposure as the same pixels would have in a final image if no changes were made in the detector, detection channel gain and offset before scanning, having the detector measure one intensity value for each pixel of the small fraction of pixels and increasing or reducing detection channel gain so that a brightest pixel in an image of the small fraction of single pixels has a value less than the maximum pixel value for a dynamic range of the detector.

2. A method as claimed in claim 1, including the steps of calculating and displaying a histogram of the intensity values of the pixels of the preview image.

3. A method as claimed in claim 2, including the steps of adjusting the preamplifier offset, if possible, to move a pixel that is the dimmest pixel in the preview image closer to a zero end of the histogram of the intensity values of the pixels.

4. A method as claimed in claim 3, including the steps of imaging multiple fluorophores, said macroscope having a detection channel for each fluorophore of said multiple fluorophores with a separate histogram of the intensity values of the pixels for each channel.

5. A method as claimed in claim 4, including the steps of imaging specimens and reducing a dynamic range to 8-bit data.

6. A method as claimed in claim 2, including the steps of providing a confocal or non-confocal imaging system using RGB brightfield imaging.

7. A method as claimed in claim 2, including the steps of conducting fluorescence imaging, requiring a sparse pixel preview fluorescence image for each detection channel.

8. A method of operating a macroscope, microscope or slide scanner to calculate, display and store as metadata information relating to a specimen by simultaneously imaging two different fluorophores, said method comprising calculating a histogram of the intensity values of a small fraction of single pixels equally spaced across a field of view that includes the entire spectrum, detecting channel gain and offset while scanning the specimen, by having a detector measure one intensity value for each pixel of the small fraction of pixels, and increasing or reducing the channel gain so that a brightest pixel in an image of the small fraction of single pixels has a value less than the maximum pixel value for a dynamic range of the detector, calculating a separate histogram of the intensity values of the pixels for each fluorophore and attaching to a final image file a histogram of pixel intensity data in that an image file.

9. A method as claimed in claim 8, including the steps of using data stored in the image histogram of the intensity values of the pixels to contract a dynamic range of the image data file after the scan is complete and providing a method of performing a contraction to start automatically before a final image is assembled.

10. A method of operating an instrument that is a macroscope, microscope or slide scanner to automatically perform a dynamic range contraction of scanned image data of a specimen, said method comprising using a preview scan histogram of the intensity values of a small fraction of single pixels equally spaced across a field of view that includes the entire spectrum or data obtained from small-area scans by having a detector measure one intensity value for each pixel of the small fraction of pixels, increasing or reducing the channel gain so that a brightest pixel in the preview image has a value less than a maximum pixel value for the dynamic range of the detector, directing a dynamic range contraction process while simultaneously calculating a new histogram of the intensity values of the pixels that describes data in the contracted file and saving the contracted file with a new histogram of the intensity values of the pixels includes as metadata.

\* \* \* \* \*